United States Patent
Schaldach et al.

(10) Patent No.: US 7,212,858 B2
(45) Date of Patent: May 1, 2007

(54) THERAPY SYSTEM

(75) Inventors: Max Schaldach, deceased, late of Berlin (DE); by Max Schaldach, Jr., legal representative, Berlin (DE); Walter Ameling, Aachen (DE); Volker Lang, West Linn, OR (US)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 391 days.

(21) Appl. No.: 10/833,385

(22) Filed: Apr. 28, 2004

(65) Prior Publication Data

US 2005/0027324 A1 Feb. 3, 2005

Related U.S. Application Data

(63) Continuation-in-part of application No. 09/603,821, filed on Jun. 26, 2000, now abandoned.

(30) Foreign Application Priority Data

Jun. 26, 1999 (DE) ................. 199 30 533

(51) Int. Cl.
*A61N 1/36* (2006.01)
(52) U.S. Cl. ............................. 607/9; 607/27
(58) Field of Classification Search .................. 607/4, 607/5, 9, 17, 27
See application file for complete search history.

(56) References Cited

U.S. PATENT DOCUMENTS

| | | |
|---|---|---|
| 4,865,036 A | 9/1989 | Chirife |
| 5,020,540 A | 6/1991 | Chamoun |
| 5,183,040 A | 2/1993 | Nappholz et al. |
| 5,421,830 A | 6/1995 | Epstein et al. |
| 5,749,900 A * | 5/1998 | Schroeppel et al. ........... 607/4 |
| 5,782,885 A | 7/1998 | Anderson |
| 5,797,399 A | 8/1998 | Morris et al. |
| 5,836,971 A | 11/1998 | Starkweather |
| 5,836,989 A | 11/1998 | Shelton |
| 5,871,507 A | 2/1999 | Obel et al. |

(Continued)

FOREIGN PATENT DOCUMENTS

DE 39 03 323 12/1989

(Continued)

OTHER PUBLICATIONS

L. Wenzel, "There is no sorcery in digital signal processing," Elektronik 23/1998, Translation of pp. 98-104.

(Continued)

*Primary Examiner*—Robert E. Pezzuto
*Assistant Examiner*—Eric D. Bertram
(74) *Attorney, Agent, or Firm*—Hahn Loeser & Parks, LLP; David J. Muzilla

(57) ABSTRACT

A medical therapy system has logic and/or signal processing stages between sensors on the input side and therapy applicators on the output side. A signal parameter is determined from the input signals using the logic/processing stages, and/or an indicator signal is determined from the input signals using a logic/processing module consisting of several logic/processing stages. The indicator signal is a measure of the probability of a future event requiring therapy, or a measure of the success of the therapy.

34 Claims, 19 Drawing Sheets

U.S. PATENT DOCUMENTS

| | | |
|---|---|---|
| 5,967,981 A | 10/1999 | Watrous |
| 5,967,995 A | 10/1999 | Shusterman et al. |
| 5,976,082 A | 11/1999 | Wong et al. |
| 6,205,357 B1 | 3/2001 | Ideker et al. |
| 6,243,603 B1 * | 6/2001 | Ideker et al. .................. 607/5 |

FOREIGN PATENT DOCUMENTS

| | | |
|---|---|---|
| DE | 196 38 738 | 3/1998 |
| DE | 198 44 296 | 3/2000 |
| EP | 0 360 412 | 8/1989 |
| JP | 06-261117 | 9/1994 |

OTHER PUBLICATIONS

L. Wenzel, "There is no sorcery in digital signal processing," Elektronik Nov. 1999, Translation of pp. 62-68.

L. Wenzel, "There is no sorcery in digital signal processing," Elektronik 13/1999, Translation of pp. 91-95.

* cited by examiner

Scenario of Congestive Heart Failure

THERAPY SYSTEM

This application is a continuation in part of Ser. No. 09/603,821, filed Jun. 26, 2000 now abandoned, which is incorporated by reference as if fully recited herein.

TECHNICAL FIELD

The invention concerns a medical therapy system, in particular an implantable system, preferably a system for electrostimulation or other treatment of the heart with electrical pulses.

BACKGROUND OF THE PRIOR ART

Systems of that kind are known, for example, in the form of implantable cardiac pacemakers, defibrillators or corresponding items of equipment for eliminating arrhythmia states of the heart or for the electrostimulation treatment of other parts of the human body.

The corresponding items of equipment generate electrical' pulses or other signals that act on the human body or provide therapeutic effects in response to signals sensed from the body. Control from the exterior is however also a possibility.

The previous devices of that kind suffer from the disadvantage that they could generally only process information in a direct relationship with the therapy; that is, information which in terms of time and also as regards processing of the signals, were very close to the direct therapy and which therefore were comparatively easy to manage in terms of the cause-effect linkage. In regard to the example of a cardiac pacemaker, this means that, to control the stimulation effect, those signals which are directly correlated with the outcome of the treatment were picked up from the heart. The simplest example in this respect is represented by a demand pacemaker which artificially produces heartbeats by stimulation whenever natural heartbeats fail. It will be apparent that here it was sufficient to have a simple timer which is resettable by a natural heartbeat in order to implement that device in regard to its basic function.

In a situation involving more complex arrhythmia states, however, the linkage relationships of signals to be picked up by sensors in the body are much more complicated.

SUMMARY OF THE INVENTION

The object of the present invention is to put to good use items of information from the body for therapy purposes, which on the one hand can be detected when relatively concealed in the signal events of the body and which on the other hand also have only a more remote time relationship with the current signal events.

That object is attained by the system according to the invention which by virtue of the time-relative linkage of system statements makes it possible to link items of information which are very far back in time and buried in a highly concealed fashion in the signal events. In this respect, it is in particular also possible to obtain and evaluate statements which are of a significance only for future system performance.

It is thus now possible for the first time in the control of automatically operating therapy apparatuses to obtain clinical indicators such a risk factors, quality-of-life indicators, and clinical consequence indicators or performance factors in the system and include them in the calculations. That is achieved by multi-stage processing which can track down, in target-related fashion, even concealed items of information in the signals picked up from the body of the patient.

Because of the time constants in the body, therapy systems should also initiate a therapy procedure as early as possible with a "lead" or "advance" in respect of time. Thus, it is possible to take action against an event which will possibly occur in the future, in such a way that the event does not in fact occur at all. In that respect, the system set forth herein enjoys the benefit that it is not bound to the procedures of conventional regulation technology, but that it interlinks statements and information of all kinds which can be expressed in a complex signal data set. As the linking effect is multi-stage, the signal information, because of the concentration of information which thus occurs, converges relatively rapidly so that a high level of reliability and security is inherent in the therapy measures obtained. By virtue of the above-mentioned concentration of information, the relatively highest-value statement is held with a time reference in each case in a module, under a verbal designation. The signal data sets in question can or must possibly also contain further details concerning the validity range thereof. They form information or statement linkages which contain a therapy condition or a mode of operation, in respect of which the statement or information in question is respectively only limitedly valid. Vectors of a kind that limit statement validity can be ancillary conditions which refer to other signal state sets or other moments in time or periodic time sequences and thus logically "bracket" them together. In that way the "context information" found can refer in subsequent processing in context (valid because condition xyz is fulfilled). In that way, in later processing it is possible to forego ascertaining the interrelating statements by virtue of processing/linking so that processing is speeded up. That applies in regard to redundant context information which therefore does not necessarily have to be present. There is however also non-redundant context information such as time references to reference time periods which form a specific time reference system, in particular, in relation to cardiac events. The reference time periods in respect of heartbeats are placed in the real time system, but hold a time vector for the next periodic event to be expected. If the heart rate then changes, that vector is changed by the corresponding linkage/processing unit, with the consequence that the corresponding reference times also alter.

What is particularly advantageous in terms of the system according to the invention is the fact that both the processing and linking or switching algorithms which determine the processing and linking or switching units, and also the signal data sets obtained in the form of linkage statements, can be exchanged over a plurality of systems. Simulations can be implemented outside the individual system. Complicated and expensive processing operations can be "taken out" by way of the communication means, or special algorithms (improvements, special solutions) can be incorporated as "plug-ins". The individual processing and linking or switching units are accessible in respect of their statement characteristics by the verbal contexts used, with which the signal parameters are occupied, without special programming knowledge, so that they can be defined by medically trained experts themselves. In that way, the high quality of the information obtained not only converges due to multi-stage intelligent linking within a system and the experience obtained over the period of time involved, but informational reliability is achieved additionally by the experience which can be obtained from the cross-linking of the experiences of all equivalent systems. In this way events which inconspicuously occur in the signal happenings can be microscopically filtered out and "amplified" to give high-grade information with a considerable decision content.

The therapy actions required are ascertained on the basis of the corresponding statement links and are defined with their corresponding reference times. If necessary conditions or secondary conditions should change, the corresponding therapy measures can be omitted if a countermeasure is initiated. Therefore, if arrhythmia or fibrillation is predicted, it is possible to initiate a multi-stage reaction if a predictor shows such an event in the future with a certain degree of probability. An initially "soft" countermeasure is triggered by the event which is to be the subject of therapy and which is indicated for a moment in time in the future under the corresponding verbal designation. Then, the continuance of the predictor is repeated by repetition of the inquiry (re-newed implementation of the corresponding linkage chain) with the current signal states which then occur. If the predictor continues, a "more severe" countermeasure is implemented on the basis of the signal states which then exist. If that does not prove successful either, then a defibrillation shock is triggered as the last countermeasure in a fibrillation procedure which is actually initiated. It will be apparent that, in regard to the signal data sets, the predictors associated with future events are variable, while clinical indicators which relate to the present are "frozen" in terms of their validity. The system therefore ascertains the therapy characteristics on a continuous basis by virtue of the inter-linked structural groups and arrives at a prediction of future events to which the current therapy is adapted. Thus the cardiac cycle is "pre-planned" in respect of time by the setting of suitable data sets for the respective reference times of real time and taking account of the phase characteristics in the cardiac rhythm. It is updated until the actual occurrence of the future events in the schedule. It is only the actual occurrence, for example, of a heartbeat that results in the actual recording thereof as a "frozen" event signal data set. A deviation between a pre-planned event and the event which actually occurred also results, by way of a suitable linking-processing unit, in a statement which provides for adjustment of a corresponding system parameter which is also retained as a signal data set.

Besides this real time-related processing, "service processing operations" such as signal compression, "compact-ing" of events which are further in the past can come to a statistical summary. In that way the data can be compressed to a greater degree, the further that they occurred in the past. It is however also possible to "take out" an uncompressed data set prior to compression thereof by telemetry so that it is possible also to have recourse in an interactive mode to the overall data set for comprehensive processing. As further "service functions", it is possible to implement stability checks and function and plausibility monitoring operations, at times when there is not a particularly high level of processing demand. That also includes checking the therapy result and a self-learning function resulting therefrom. It will be apparent that experiences of that kind can also be put to use for other similar therapy apparatuses by telemetry and communication with corresponding centers.

In regard to details, attention is directed to the accompanying claims.

BRIEF DESCRIPTION OF THE DRAWINGS

Advantageous developments of the invention are moreover characterized in the appendant claims or are set forth in greater detail hereinafter together with the description of the preferred embodiments of the invention, with reference to the drawings in which:

DETAILED DESCRIPTION OF A PREFERRED EMBODIMENT

Figure 1:
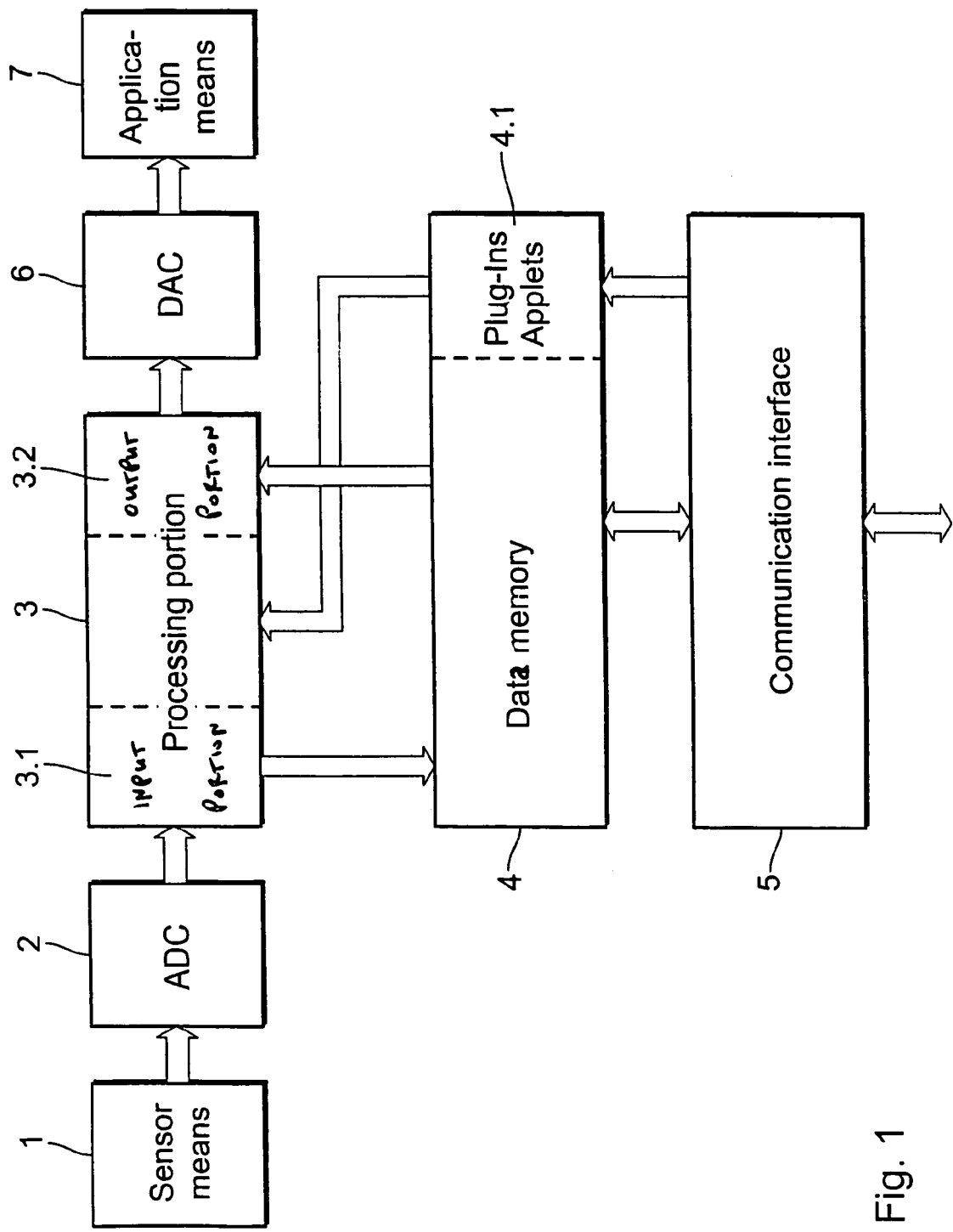
FIG. 1 shows a general overview in the form of a block circuit diagram of the heart stimulation system according to the invention.

The general overview shown in FIG. 1 of the therapy system according to the invention shows the fundamental structure thereof. Described here are the physical main or basic units which are used for implementation thereof. The elements described in the structural groups illustrated hereinafter are in contrast more function-related and set out the mode of operation in detail. The illustrated therapy system is an implantable system for eliminating cardiac arrhythmias by electrostimulation or stimulation shock application as is known as a cardiac pacemaker or an ICD (implantable cardioverter defibrillator).

The interface to the patient is formed by a number of sensors which are combined in the drawing as sensor means 1. The individual sensors in that respect may be physical or chemical converters or transducers which pick up signals on the body and convert them into time-dependent electrical signals. The converters or transducers typically form electrodes or other signal generators which permit a statement about the condition of the patient. The electrical signals are fed to analog-digital converter means (ADC) 2. The digitized output signals thereof go to a processing portion 3 formed by a data processor which is in interacting relationship with a data memory 4. The processing portion 3 has access to a data memory 4, which contains both the patient condition data characterizing the patient and also system condition and system configuration data describing the system associated with the patient. The processing portion 3 is priority controlled and therefore executes the pending signal processing operations according to the urgency thereof. This processing takes place in real-time in relation to an input portion 3.1 and an output portion 3.2, as the corresponding input and output signals must be picked up and made available in true-time fashion. The rest of the processing, in contrast, can be decoupled with respect to time and can thus be effected according to the degree of urgency, wherein certain processing tasks of a more complex nature can be implemented in time-displaced relationship or in an externally networked mode, as is described in greater detail hereinafter.

The output portion 3.2 of the processing portion 3 is connected to digital-analog converter means 6 forming the interface to therapy applicator means 7 which act on the patient. This involves the actual therapy surface in the form of electrodes or chemical metering devices.

System condition and system configuration data, including the associated linking and processing algorithms, can be "post-loaded" into the processing portion 3 from the exterior.

Additional system configuration data of that kind are held in the plug-in portion 4.1 of the data memory 4. The content of the data memory 4 can be read out externally by way of the communication interface 5 or altered from there. In that way it is possible both to bring out the processing of data and also to supply external system condition and system configuration data as well as collections of patient data and generalized patient condition parameters. The priority-related processing procedure makes it possible, in the context of a processing operation of low priority, when involving a low level of other processing incidence, also to manage precautionary calculations which are possibly required but which otherwise can also be discarded.

Storage of the data is effected in so-called signal data sets, as groups of mutually associated items of information. Those signal data sets have time mark and context signals, as will be described in greater detail hereinafter.

Figure 2:
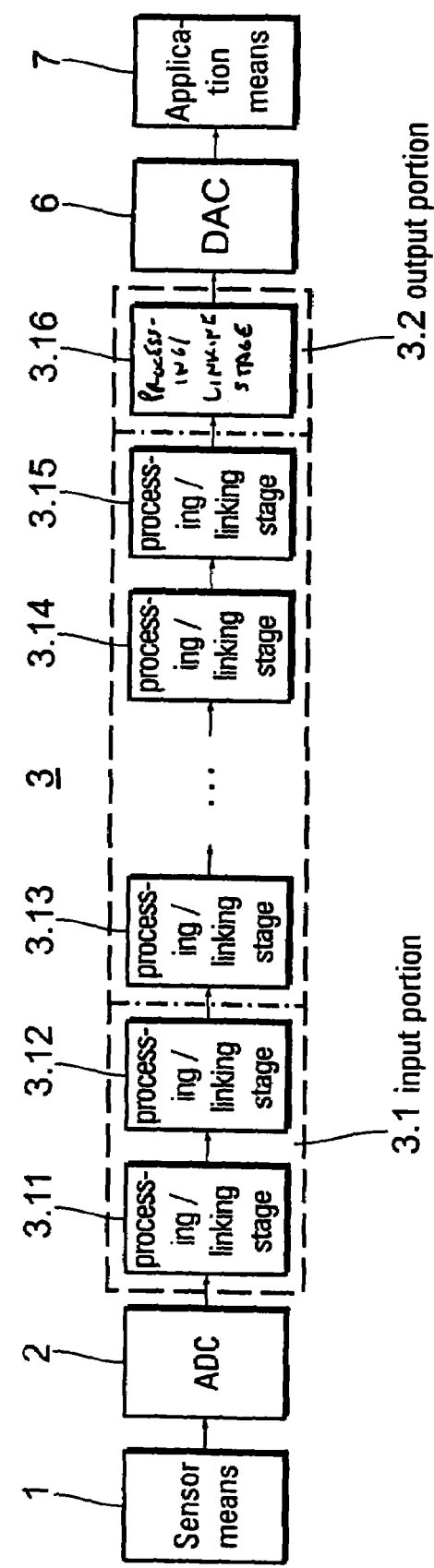
FIG. 2 shows an embodiment of the processing portion as a detail of the FIG. 1 structure in simple form.

FIG. 2 is a view in greater detail showing the configuration in principle of a simple signal processing procedure with unlinked processing from the sensor means 1 to the applicator means 7. The arrangement of the analog-digital converter means 2 and the digital-analog converter means 6 corresponds to that shown in FIG. 1. In this case however the processing portion 3 of FIG. 1 is reproduced in the form of successively connected blocks.

In this case, at least one digitized sensor output signal is fed as an input signal successively to two first (upstream-connected and downstream-connected) processing/linking stages 3.11 and 3.12. The processed sensor signal forms the sensor signal of the downstream-connected first processing/linking stages 3.12. The two first processing/linking stages 3.11 and 3.12 jointly form a stage for pre-processing of the sensor signals. That pre-processing serves in the first stage for geometry evaluation. As a result, for example in the case of cardiac stimulator systems, it is possible to implement objectivised processing of signals which originate from different electrode configurations. Output signals from interconnected arrays of a plurality of electrodes are possibly linked or switched in this stage. In the downstream-connected one of the downstream-connected first processing/linking stages 3.12, time-frequency evaluation of the sensor signal or other signal evaluation is possibly effected. That signal evaluation operation is initially only related to the current sensor signals themselves. It corresponds to short-time evaluation or filtration in order to compensate for fixed interference or transit-time influences which are not dependent on other signals or system states. That compensation procedure, however, also embraces the sensor signals with each other. This description describes hereinafter how that processing, on the basis of the further features of the system described herein, can also be implemented in linked relationship with other signals and in a time-iterative procedure. This processing portion was identified in the structural group 3' as the input portion 3.1.

The processed sensor signal as the output signal of the first processing/linking stage 3.11/3.12 forms the input signal of at least two further processing/linking stages 3.13 and 3.14, which from the processed sensor signals produce a control parameter for the application means or a clinical observation parameter or predictor as an output signal of the second processing/linking stage. The difference is that the direct control parameters (for example missing heartbeat in the case of a pacemaker) are directly formed as hitherto. A clinical observation parameter or predictor in contrast involves a concealed signal state which is picked up by the sensor means and which, picked up in time-displaced relationship, is subject to a longer processing time and is possibly picked up iteratively and/or in the context with other signal states. It is of significance, in regard to the present system, that the indicator or predictor signals are processed with the same system structure as the direct control signals, thereby affording a substantial simplification in control complication and expenditure. The predictor signals differ from the indicator signals in that they include a specific future expectation period of time for a future patient condition while an indicator signal is associated with a time range which is not defined in detail and which begins with the establishment thereof. Processing of the time conditions is set forth in greater detail hereinafter.

The at least one control signal, a clinical indicator or predictor, forms the input signal of a third processing/linking stage 3.15, which produces a therapy applicator crude or basic signal as the output signal of the third processing/linking stage. That stage provides for conversion of the indication or prediction in linking relationship with a control signal into a signal which as a therapy applicator crude signal forms the basis for the treatment.

The therapy applicator crude signal serves as the input signal of a fourth processing/linking stage 3.16 which produces a processed therapy applicator input signal as the output signal. This fourth processing and/or linking stage includes geometry evaluation of the therapy applicator means of the therapy applicator crude signal, which includes adaptation to the geometrical arrangement of the application means.

The mode of operation of the individual blocks is set out hereinafter. The arrangement shown is symbolically functional as real processing can be effected in time-sequential and iterative mode. The illustrated functional block-wise combination of the processing structures is however of significance.

Figure 3:
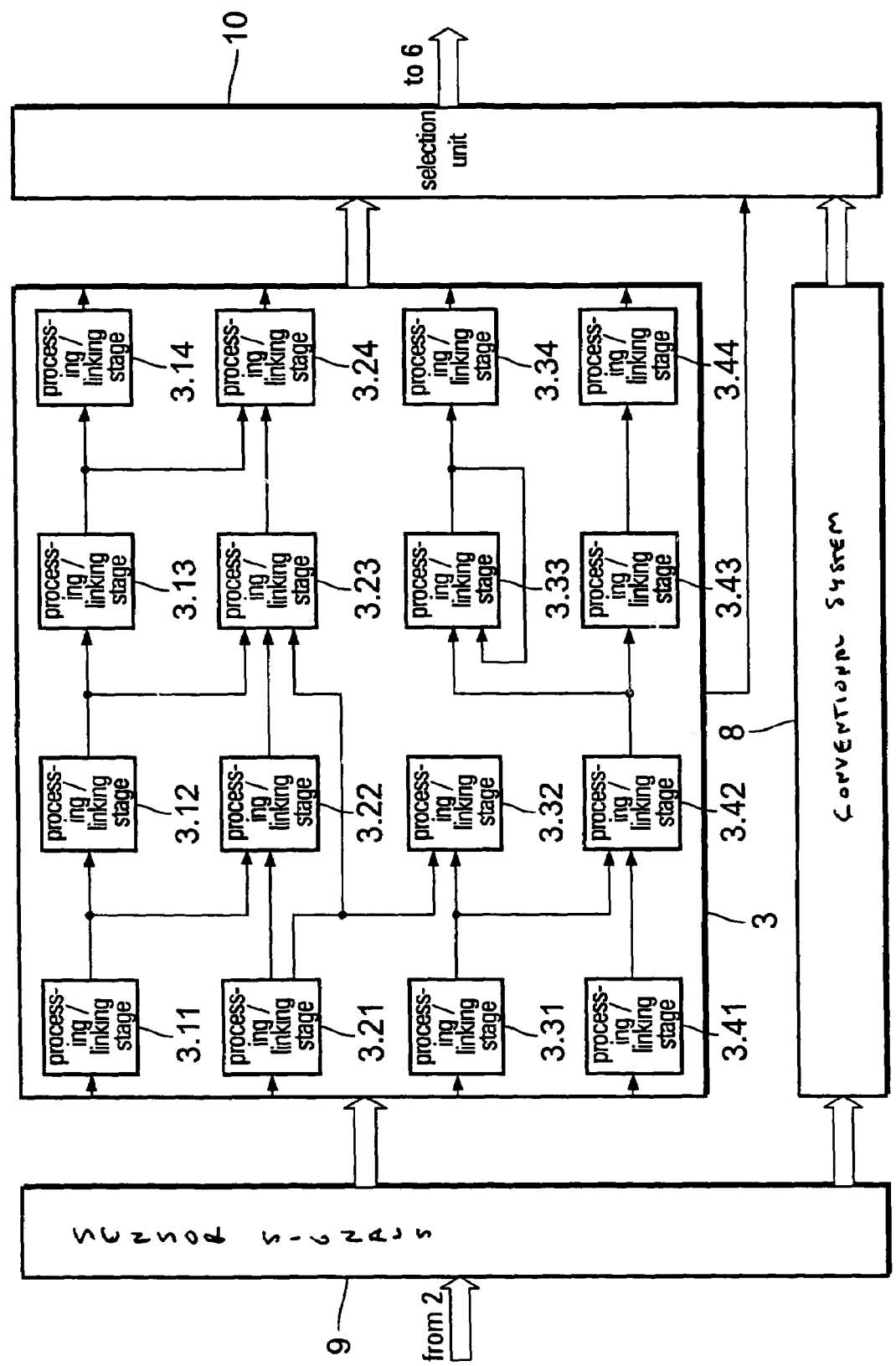
FIG. 3 shows an embodiment of the processing portion as a detail of the FIG. 1 structure in more complex form.

The processing portion shown in FIG. 3 is of a more complex structure than the simplified embodiment illustrated in FIG. 2. What is shown herein is the way in which a networked structure can be used, instead of a purely serial processing structure. The arrangement now has four series of processing and linking stages 3.11 to 3.14 etc., 3.41 to 3.44, which respectively have four structural groups. In this respect, each structural group includes a signal output. The number of inputs varies. It will be apparent that various output signals can also be fed from stages which are further back to a subsequent processing and linking stage (example: processing/linking stage 3.23). It is also possible for the output signal of a stage (example: processing/linking stage 3.33) to be returned to itself for iterative processing purposes. It will be apparent that each illustrated processing stage furnishes a signal data set which contains information in the form of a signal data set which is compressed in a kernel or core statement which can be subjected to further processing in the subsequent stages. That kernel statement is combined with a time reference for the validity thereof and contains a statement about a previously found signal state, a diagnosis and a therapy measure which is to be initiated in relation thereto. That can easily involve Boolean expressions such as simple yes-no decisions or amplitude values. It is however also possible in a corresponding fashion for signal configurations or spectra to be contained in the signal data set. These are those respective items of information which can be the basis of more extensive decisions which result in statements of higher value. In that respect, the items of information are linked in accordance with their validity in respect of time and their designation, so that at any time it is also possible to obtain statements for a performance at other reference times if the corresponding time reference is selected.

In FIG. 3, a conventional system 8 is additionally provided as backup. A sensor data branching or distributing unit is connected downstream of the analog-digital converter 2 which receives its input signals from the sensor means 1 (see FIGS. 1 and 2). The sensor signals 9 are passed both to the conventional processing portion 8 and also to the processing portion 3 which operates on the basis of the principle of the invention. The linking and processing stage 3.32 is for plausibility checking. In the event of absent plausibility in respect of a monitoring signal condition, in the processing portion 3, outputs a control signal and the selection unit 10 which in this case converts the output signals of the conventional processing unit 8 which then actuate the application means 7 by way of the digital-analog converter group 6.

Figure 4:
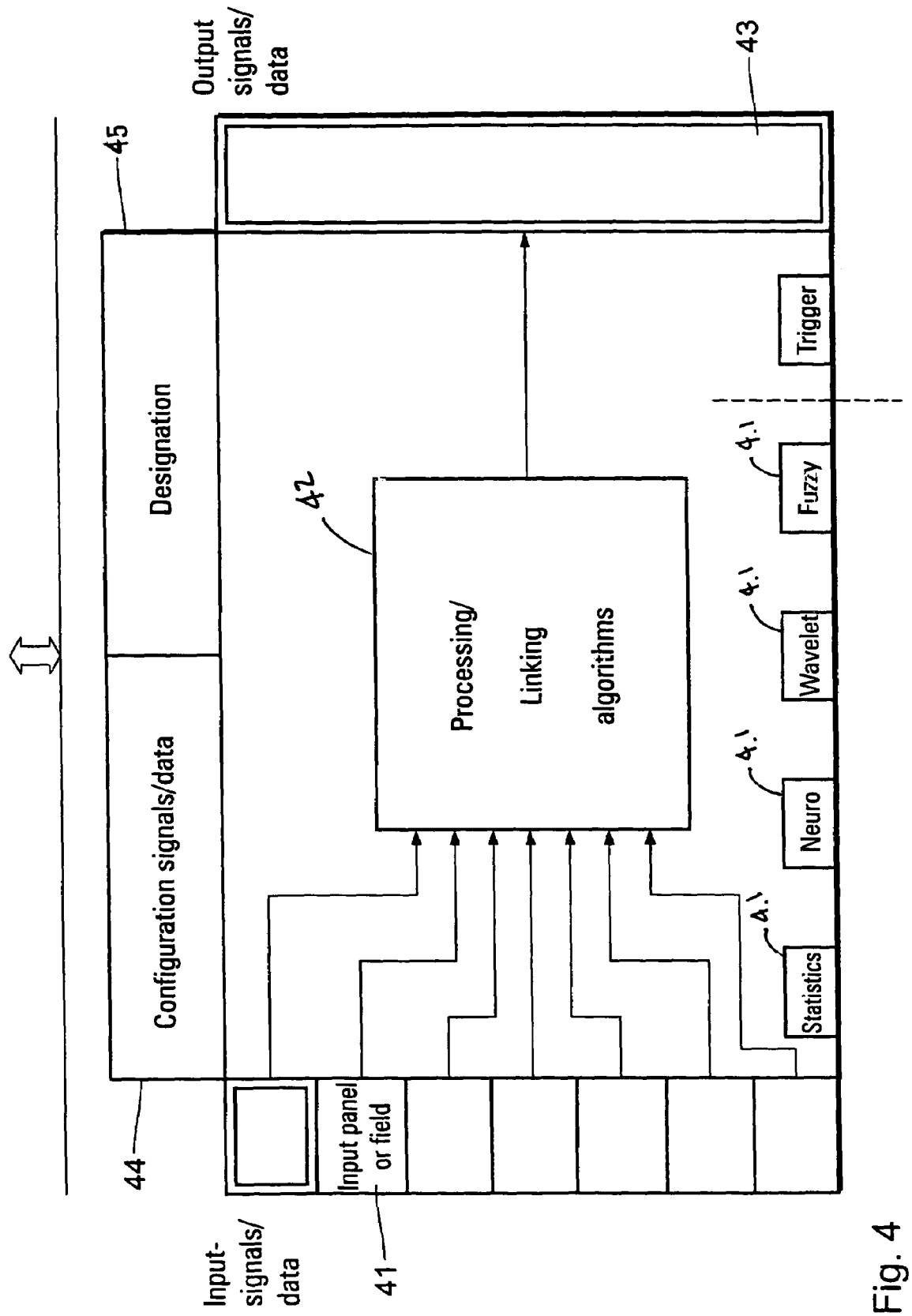
FIG. 4 shows a linking/processing stage as a detail of the processing portion.

The block circuit diagram shown in FIG. 4 illustrates in detail the structure of a single linking/processing stage 3.11. This forms the physical computing unit which in a program-controlled manner executes the processing operations and in so doing has recourse to the parameters in the data memory. Reference numeral 41 denotes input panels or fields for reading in the data memory 4, by way of the identifications and time marks thereof, the input signal/signal data sets selected by the conditions retained in the memory for the linking and processing algorithm 42. The data to be processed are then transferred to the output data field 43 and provided for further processing for the subsequent stages or transferred into the data memory 4 together with the time mark. The linking/processing algorithm is determined by the configuration signal data set 44 which is also contained in the data memory 4 in association with the designation 45 of the processing and linking stage in question. Processing is triggered in each case by the appearance of or the change in an input signal/data set in an input panel or field 41, if all time references of the input signal/data set are valid, i.e., they contain as a validity range the real time which occurs at the terminal. Unconditional signal processing independently of real time can be forced by a particular trigger condition by way of the time input if here a time which does not correspond to a real time is communicated. Service operations can be regularly forced from the exterior by way of trigger conditions of that kind (for example in dependence on the system loading, if for example there is in the data memory 4 no signal/data set which contains a time reference which is disposed less than a predetermined time difference before the real time).

As shown in FIG. 1, plug-ins 4.1 are available from the exterior by way of the terminals for the linking/processing algorithm, which plug-ins support the linking/processing algorithm by virtue of computing procedures which can be used in conjunction with said signal linking. This generally involves mathematical procedures which make it possible to achieve a statement with a relevance which is high in the context in question, by virtue of suitable information compression. That includes statistical processes, neuro processes, wavelet processes, fuzzification processes and statistical mechanics processes. Some of these processes are illustrated in more detail in FIGS. 7C through 7G.

The output signal/data set can therefore, at the preselected time, start up both further data operations in other linking and processing stages and also the applicator means.

Signal data sets are processed in relation to a reference moment in time or a reference time range. A signal data set is comparable to a status vector and is stored in the form of an information unit in the data memory. The signal data set as an information unit is identified by its designation and a time detail which determines its validity. That can be a moment in time or a time range which is possibly open upwardly to await further valid signals, i.e., it does not involve an end moment in time. All signal data sets with the same designation form a data set which characterizes the pattern or configuration with respect to time of the signal data set in question. The signal data sets can contain signal spectra, geometrical forms as signal amplitude patterns, fixed values, vector references to other signal data sets on the basis of their designation or validity time. It is also possible to provide a weighting parameter which includes an evaluation of the statistical certainty of the signal data set for further processing.

The signal/data sets therefore describe both the patient condition and also the system condition in their entirety in order to guarantee operation of the system. All condition signals are brought together for processing, compared or logically linked in order to initiate a therapy action which is also retained as a condition set. The signal data sets form the events which identify the system and the patient, wherein the conditions are also variable in respect of time and are retained as events of that kind.

A signal data set is respectively associated with a linking and processing stage of the same name. It describes the signal which occurs at its output.

In that respect, the signal data sets are associated with respective conditions with the relatively highest relevance. These are conditions which determine as clearly as possible and without redundancy the characteristics of logically dependent conditions (in the present system those which are associated with subsequent linking and processing stages).

The signal data sets do not need to contain entirely all the stated signal parameters, but only have those which are relevant for the linking and processing stage in question.

The signals of the sensor means and the therapy application means are also described by signal data sets.

In accordance with the signal data sets, the data memory retains configuration signal data sets which for the linking and processing stages, in association with the designations thereof, record the linking and processing algorithms thereof. The linking algorithms contain the designations of the preceding sensor means whose signals are processed in the respective linking and processing stage and the algorithm which is to be applied in the linking procedure. The processing algorithm is also recorded. The signal spectra and amplitude configurations or patterns of the signal data sets describe their transmission characteristics as in system theory signals and system performance (for example, in the form of the jump answer) can be mathematically described in a similar manner.

There are also geometry signal data sets which provide a geometrical correction for the signals of the sensor means and therapy application means corresponding to the spatial distribution thereof in the body. Thus, the common signals from electrodes in the case of electrostimulation, for example, form overall a signal image which is to be broken down for the individual electrodes into its corresponding components. That component break-down depends, however, on the geometrical electrode configuration where the corresponding configuration is produced by the geometry signal data set.

All signal/data sets in the memory can be transmitted to the exterior and conversely read in from there. In that way, a communication to the exterior is possible and corresponding processing can take place.

The same applies in regard to the system configuration data.

Figure 5:
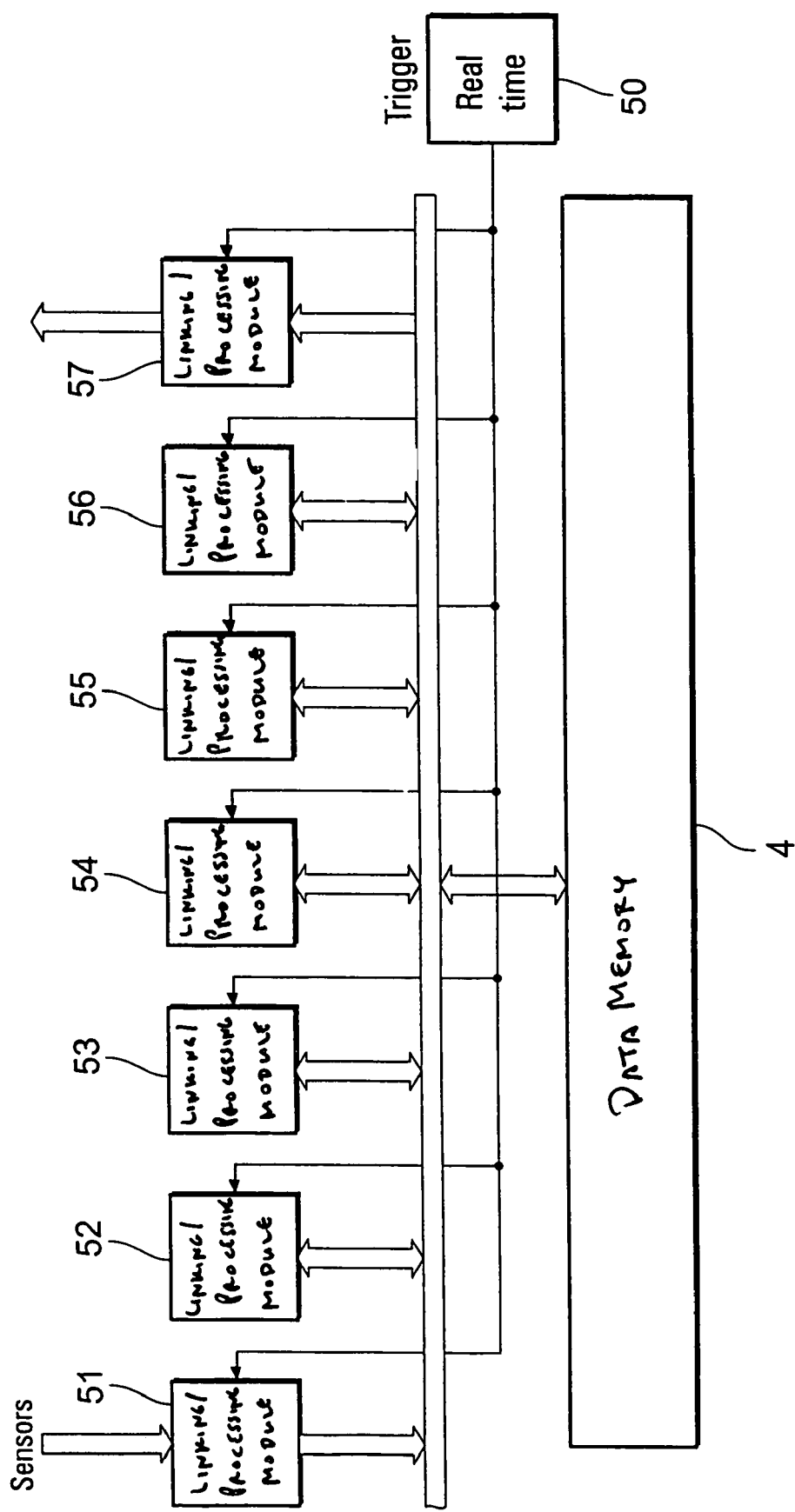
FIG. 5 is a view of a number of function-related linking/processing modules which each contain a number of linking/processing stages.

In the view shown in FIG. 5 the processing portion is, for example, diagrammatically subdivided into a plurality of groups which can contain, in functionally related form, complex linking and processing units, which in turn can be of a more complex structure and internally include a whole series of linking and processing stages, as is shown in FIG. 4. Linking/processing modules of a complex structure of that kind, in contrast to individual linking and processing stages, may therefore include a plurality of outputs. That however is not necessarily the case. They behave like composite linking and processing stages, but they are not so variable and transparent in terms of their actuation because they execute fixed functions which are not to be accessible or variable in order not to endanger the operational reliability and security of the system by virtue of wrong manipulations. Thus, it is possible, for example, for a complete conventional cardiac pacemaker function to be incorporated into a complex linking/processing module of that kind, in which case that system puts its one number of signal data sets with designations and the reference times in question into the data memory and makes them available there for the rest of the system. By way of "handles" which form signal data sets, the corresponding linking/processing modules can be addressed both by linking and processing stages and also from the exterior. The linking/processing modules which in that way can simulate the performance of known therapy apparatuses can then be programmed in accordance therewith, in which case the programming inputs can be established by way of linking and processing stages. That has the advantage that systems which are familiar to the doctors can be implemented as such and therefore do not unnecessarily complicate the structure which can be influenced and viewed from the exterior by way of telemetry means. The operators can therefore concentrate on those systems and properties which must be open to therapeutic attention, for example, because they involve measures or properties, the effect of which on the patient cannot be completely sure.

The illustration in FIG. 5 shows a plurality of such linking/processing modules (hereinafter also referred to briefly as "modules") 51 to 57 which interact with the data memory 4. The view shows a basic module 51 which acquires input data obtained from the sensor means and ascertains, for example, the application times for the basic therapy, and further modules 52 to 57 of which the module 57 actuates the application means, in which respect in this case various predetermined therapy patterns can be called up by way thereof. The call-up procedure is once again effected by the real time or an internally set cycle time reaching a predetermined present time which is set by another module, attainment of the predetermined time then acting as a "trigger" (block 50), as described above.

The functions of the other modules 52 to 56 can be selected to be various functions. Set out as an example hereinafter is a series of complex functions which can be executed by linking/processing modules:

Various time or event-triggered functions can supplement the mode of operation of the basic module 51. In that respect, a module of that kind can be transparent, in particular regarding its internal structure, e.g., it can be designed to be accessible from the exterior, with respect to all of its linking and processing stages (see FIG. 3).

Compacting of data in the memory, in the sense of signal compression. Instead of the individual signals which are recorded with respect to their amplitude pattern or their spectral properties in association with the respective time references, the events are only recorded and classified as event numbers for respectively associated periods of time (histograms) or are recorded in another form as signal statistics.

Figure 6:
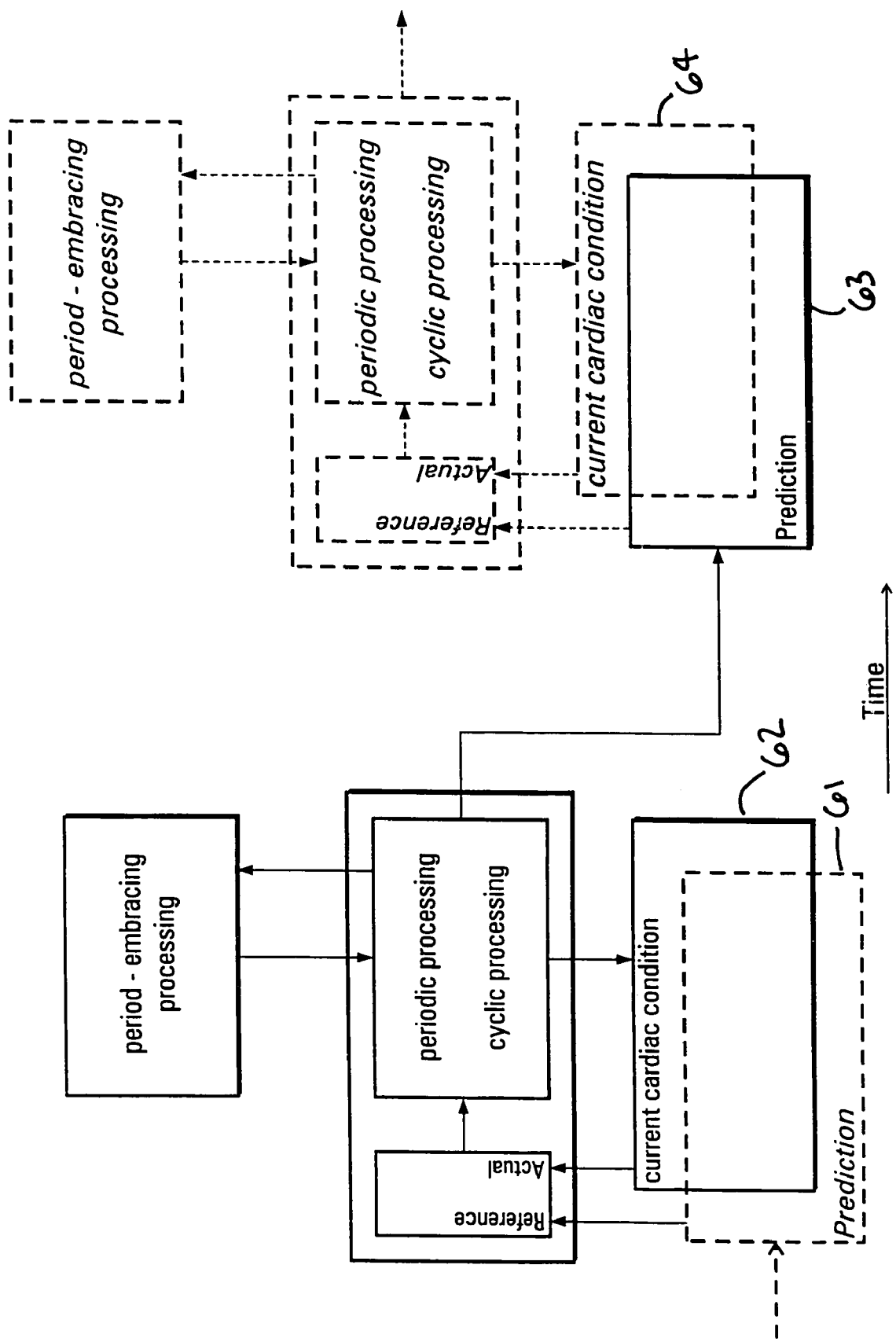
FIG. 6 shows a view of a prediction model in accordance with the principle of the invention.

FIG. 6 diagrammatically shows how, with the system according to the invention, the prediction produced on the basis of the indicators is compared to the condition which actually occurs, and a reference value-actual value comparison is implemented on the basis thereof. Specifically, a first prediction 61 of the cardiac condition is derived from an initial data set and compared at a first time against a set of parameters constituting a current cardiac condition 62. By processing these data with the mathematical tools available, including periodic embracing processing, periodic processing and cyclic processing, a second prediction 63 of the cardiac condition, this being for a second time later than the first time, is ascertained. At the second time, the second prediction 63 is compared against the then-current cardiac condition 64, and the process is repeated on a sequential basis, although only these first and second iterations are shown in FIG. 6.

Figure 7A:
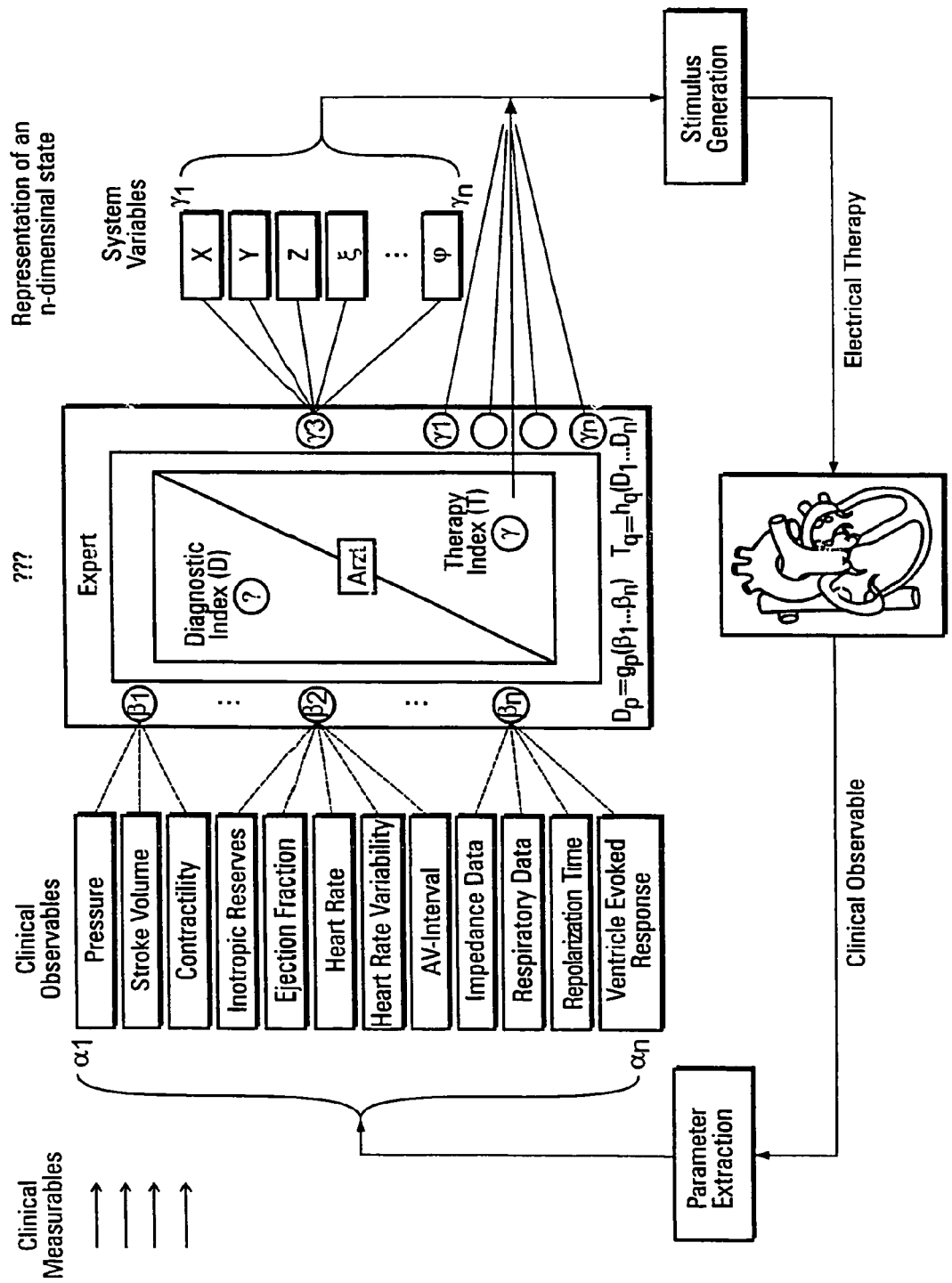
FIGS. 7A–7M show 13 views in relation to the functionality of various systems or system portions designed in accordance with the concept of the invention.
Figure 7B:
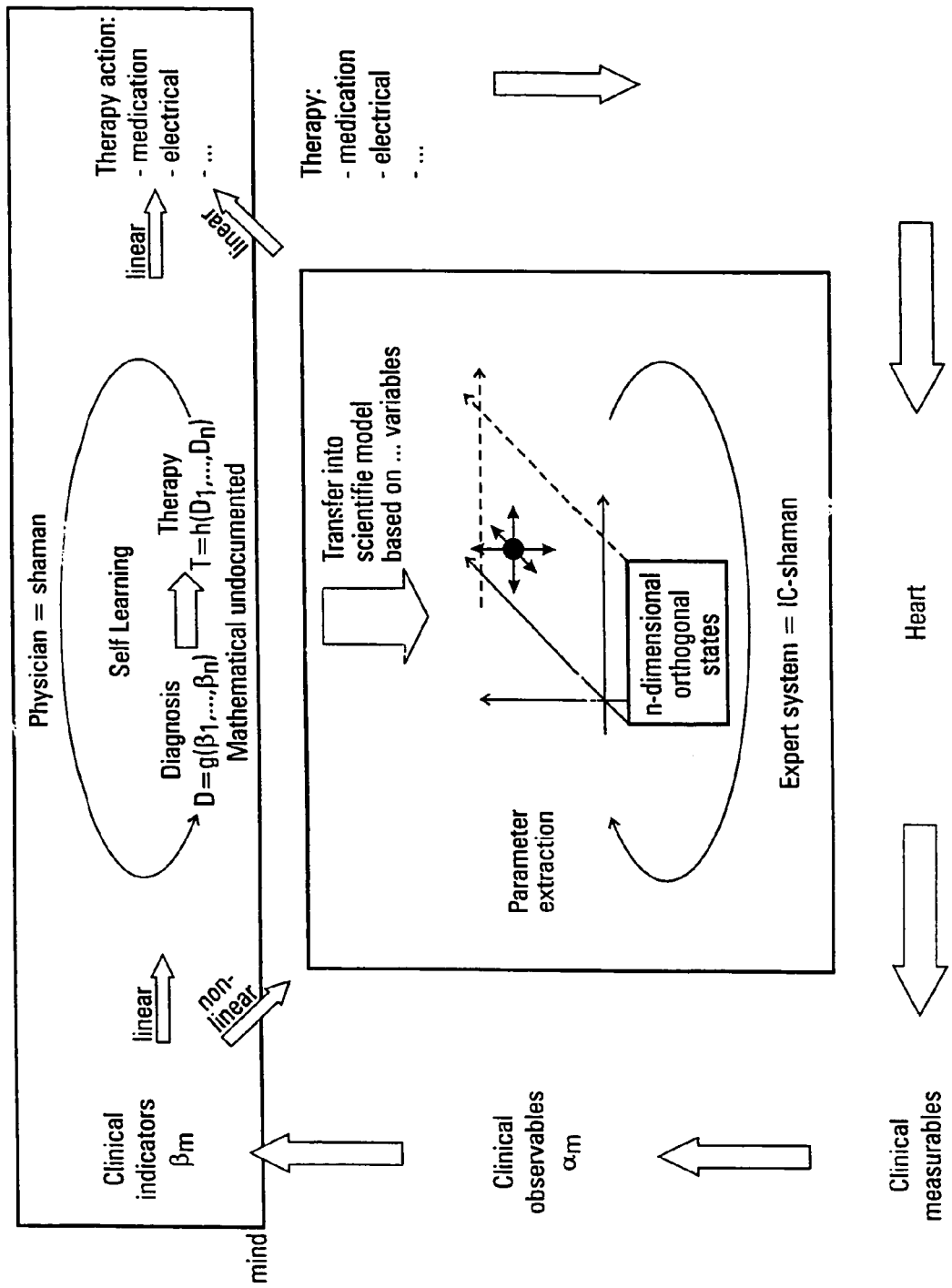
Figure 7C:
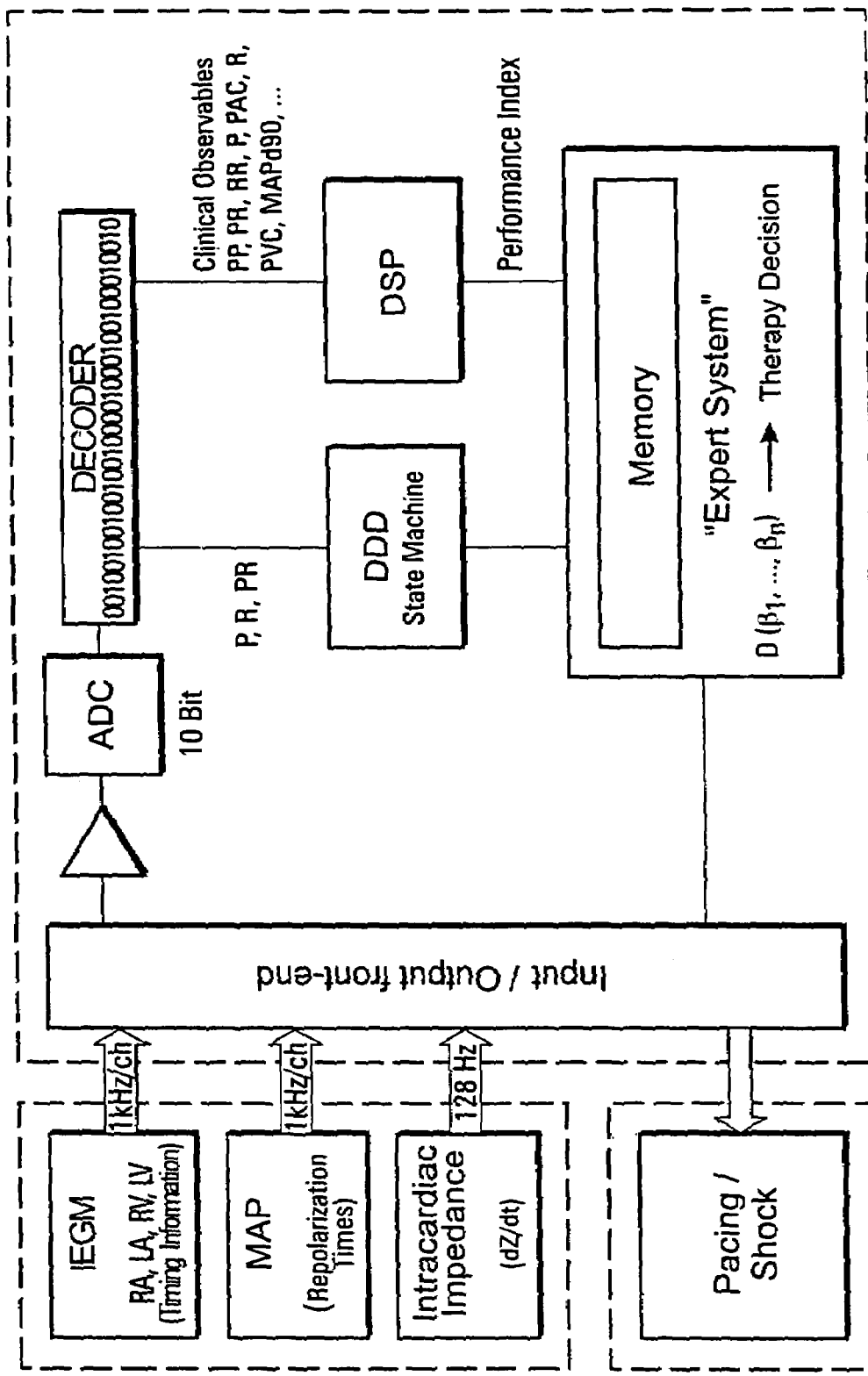
Figure 7D:
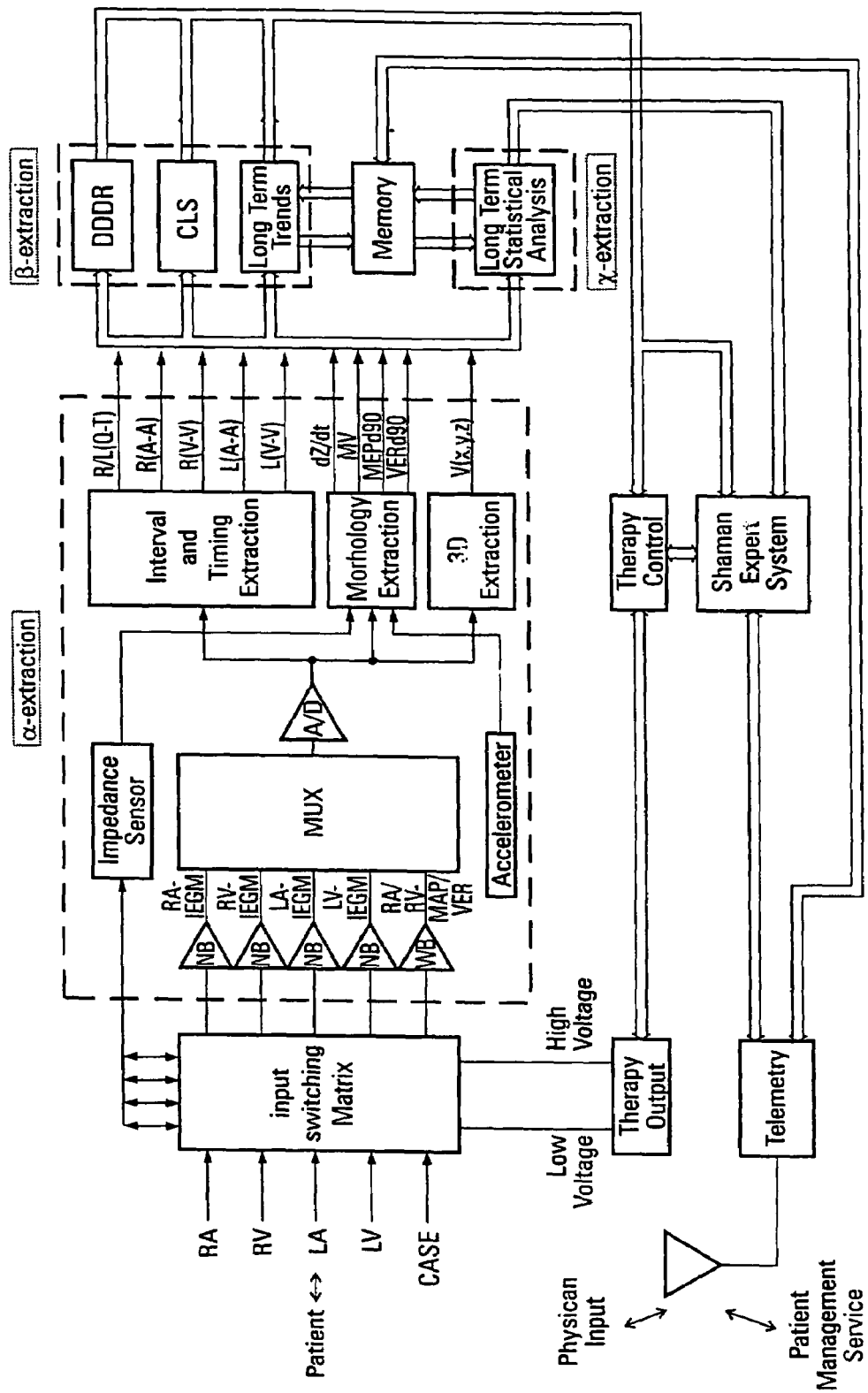
Figure 7E:
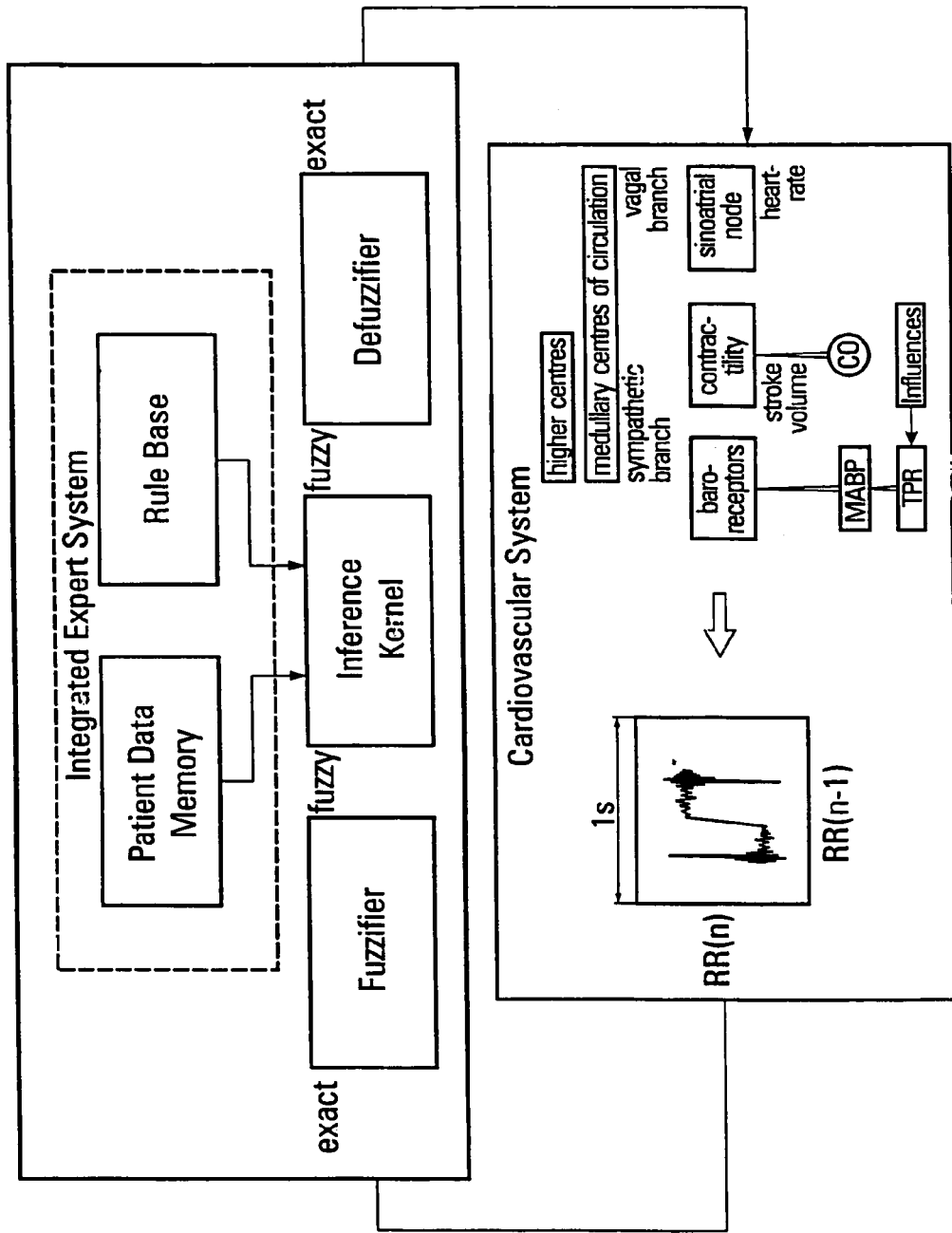
Figure 7F:
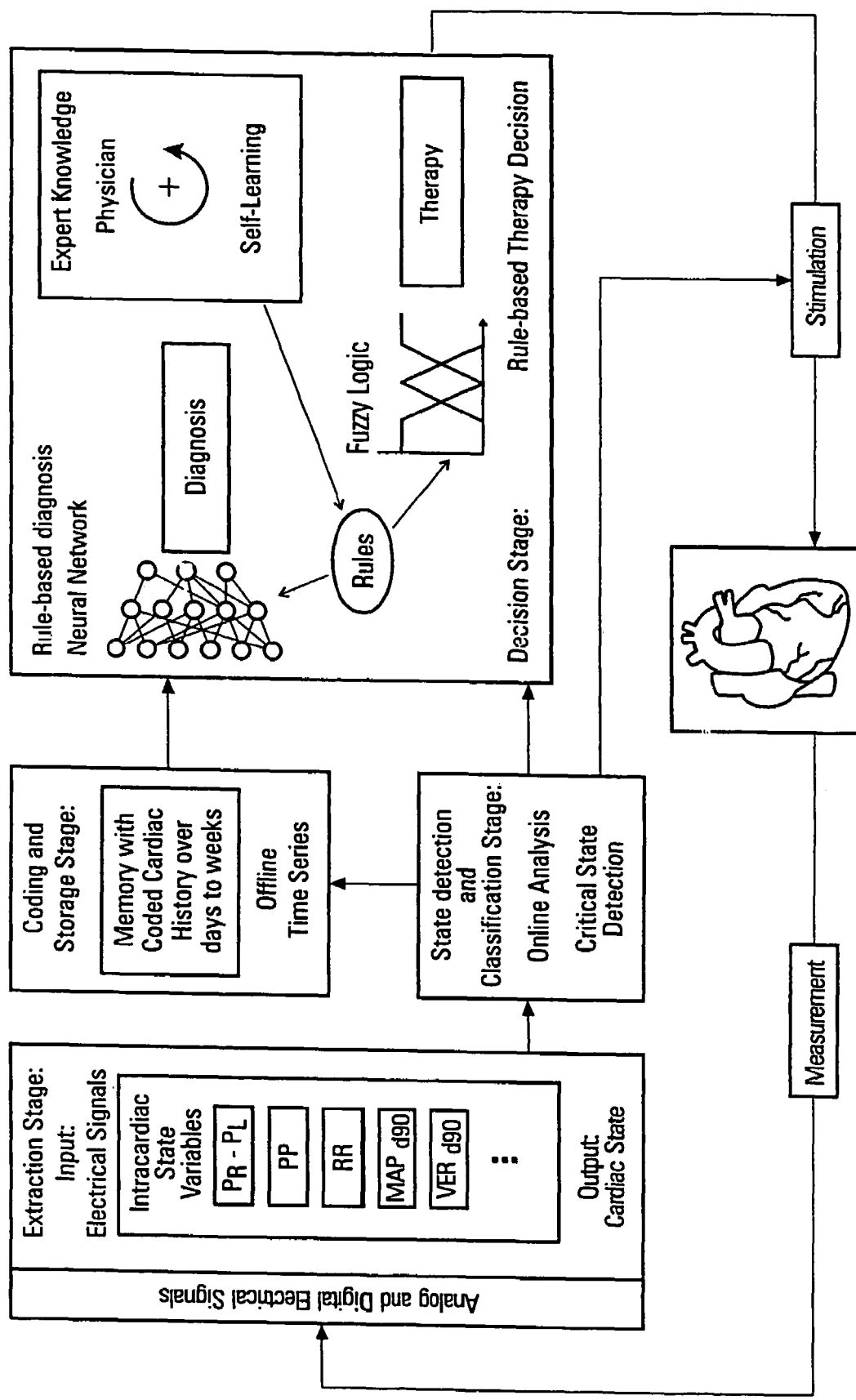
Figure 7G:
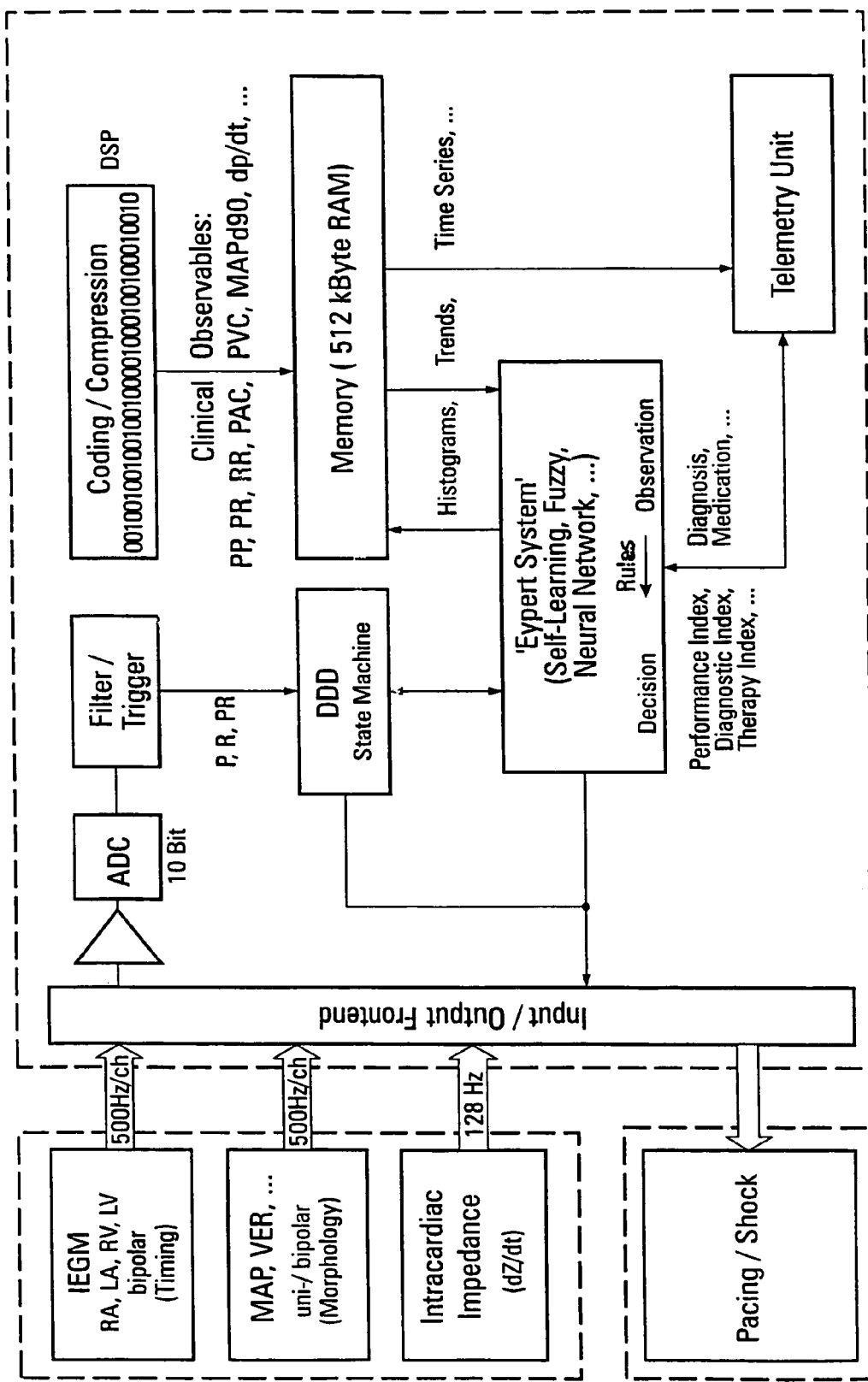
Figure 7H:
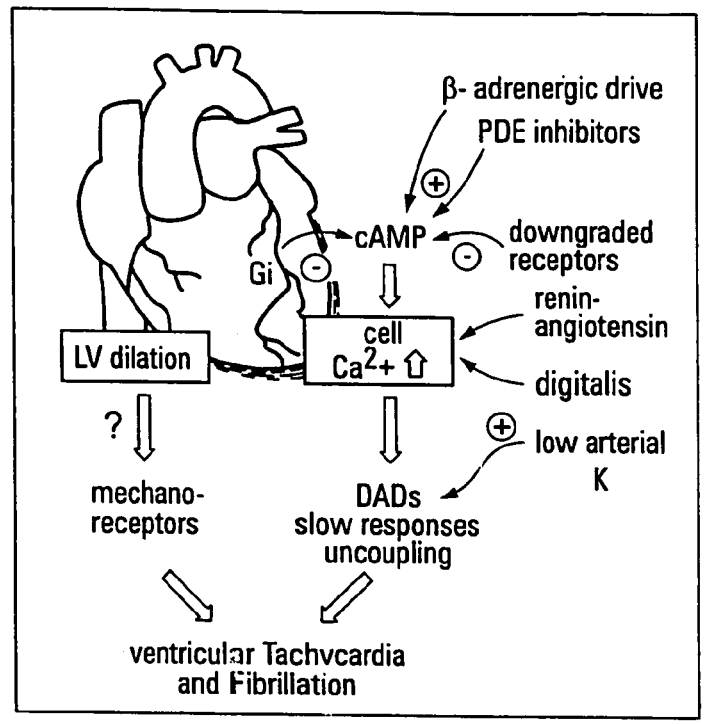
Figure 7H:
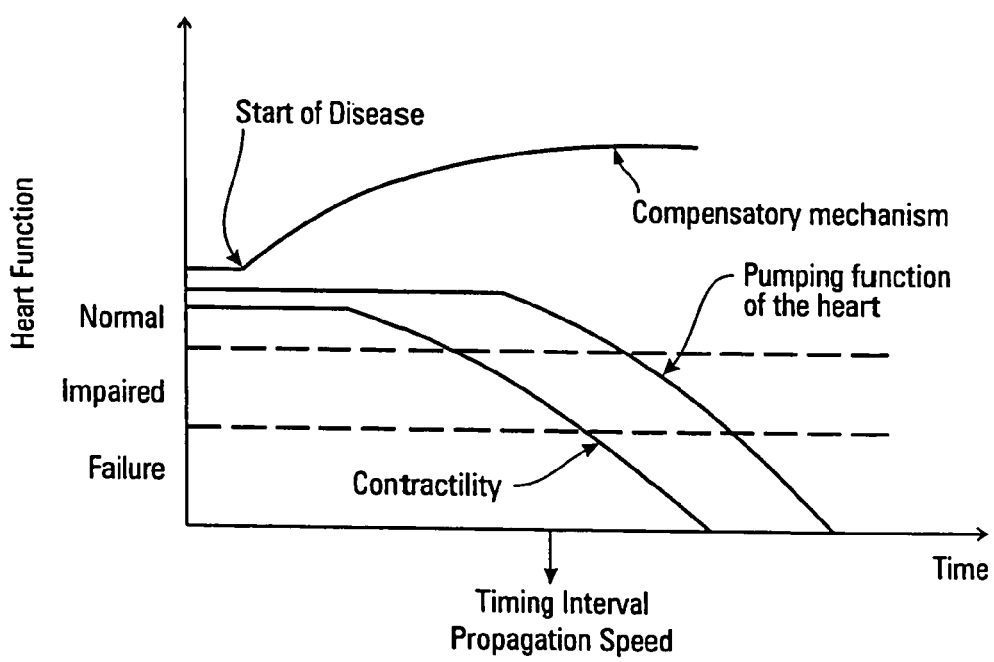
Figure 7I:
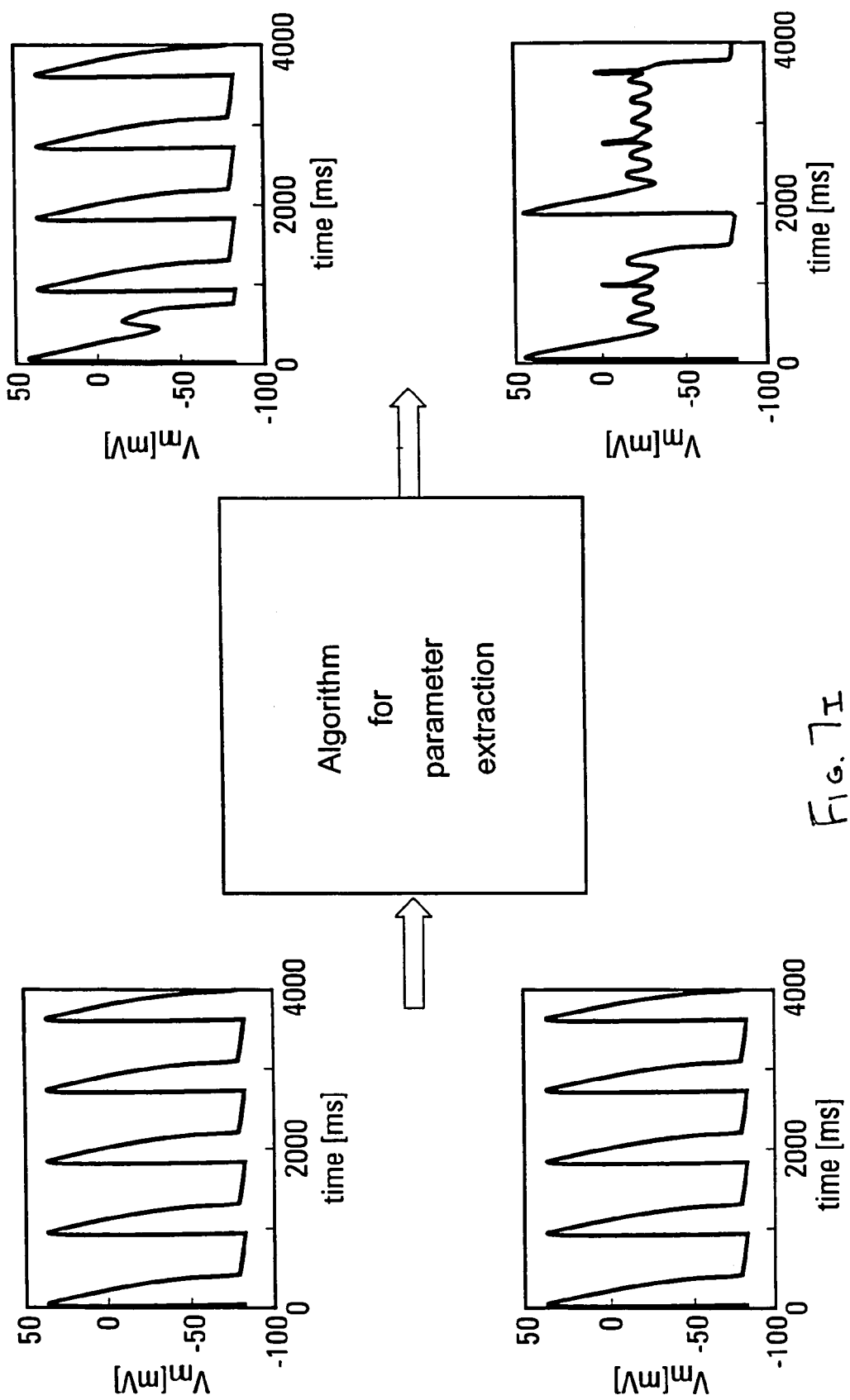
Figure 7J:
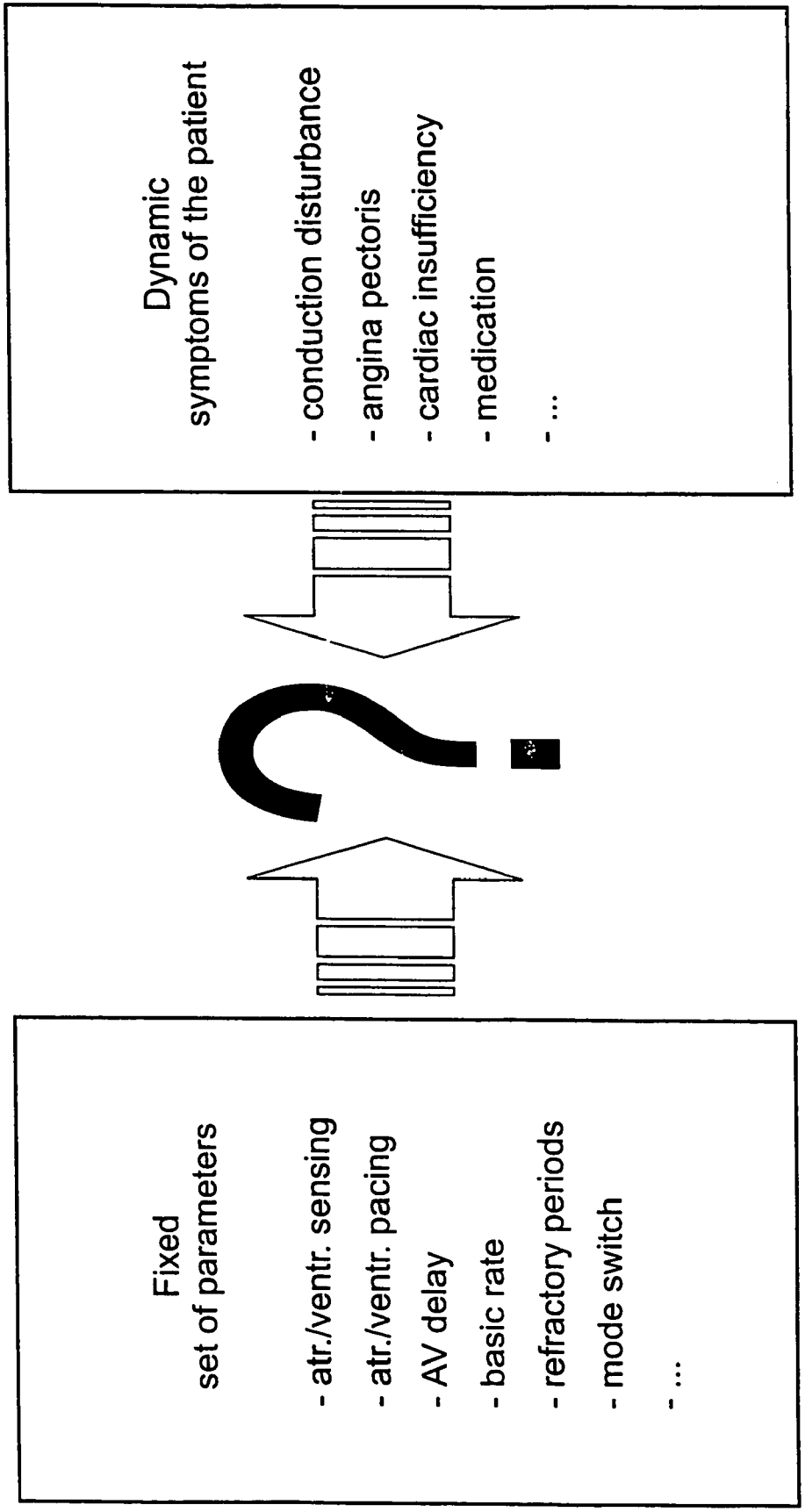
Figure 7K:
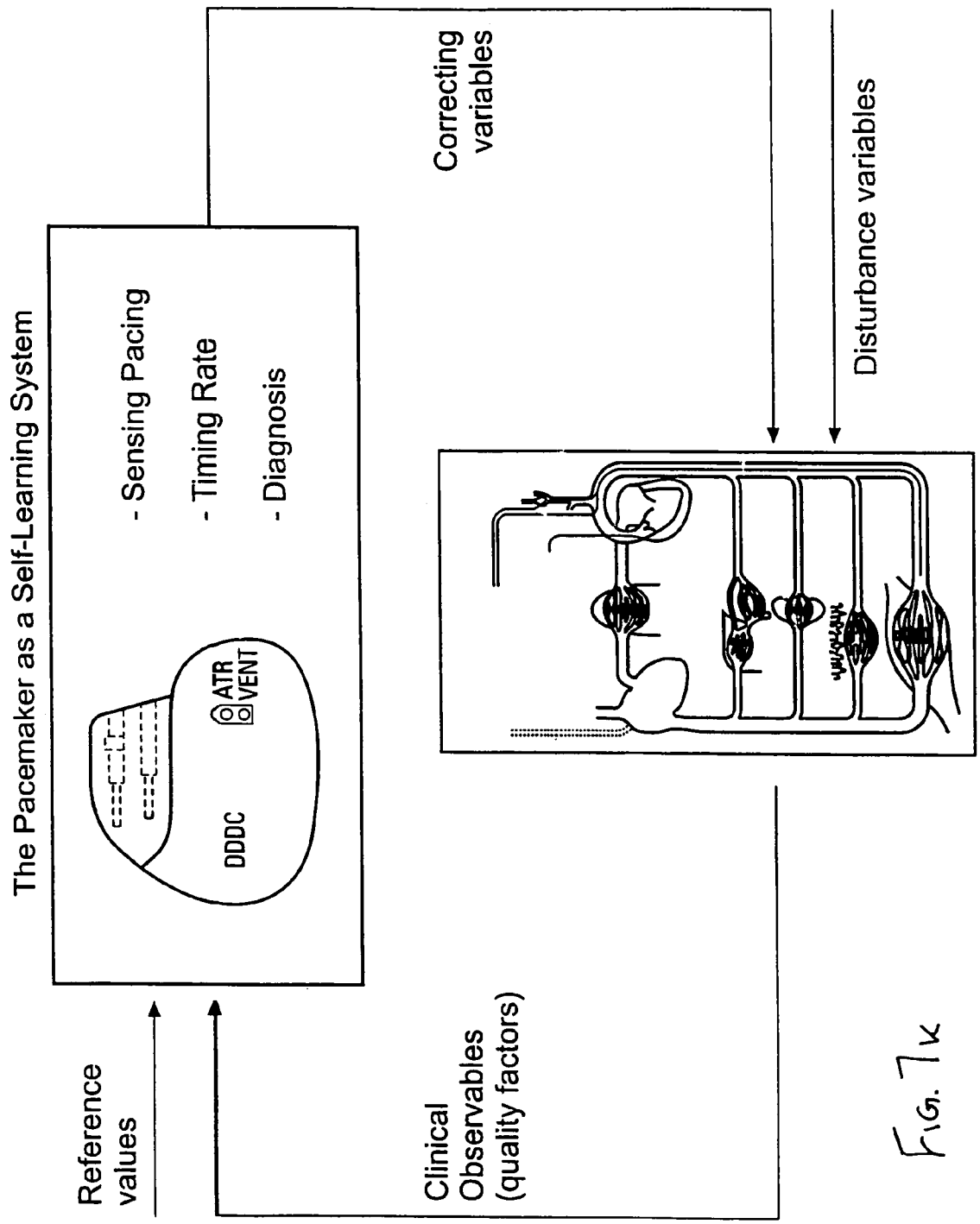
Figure 7L:
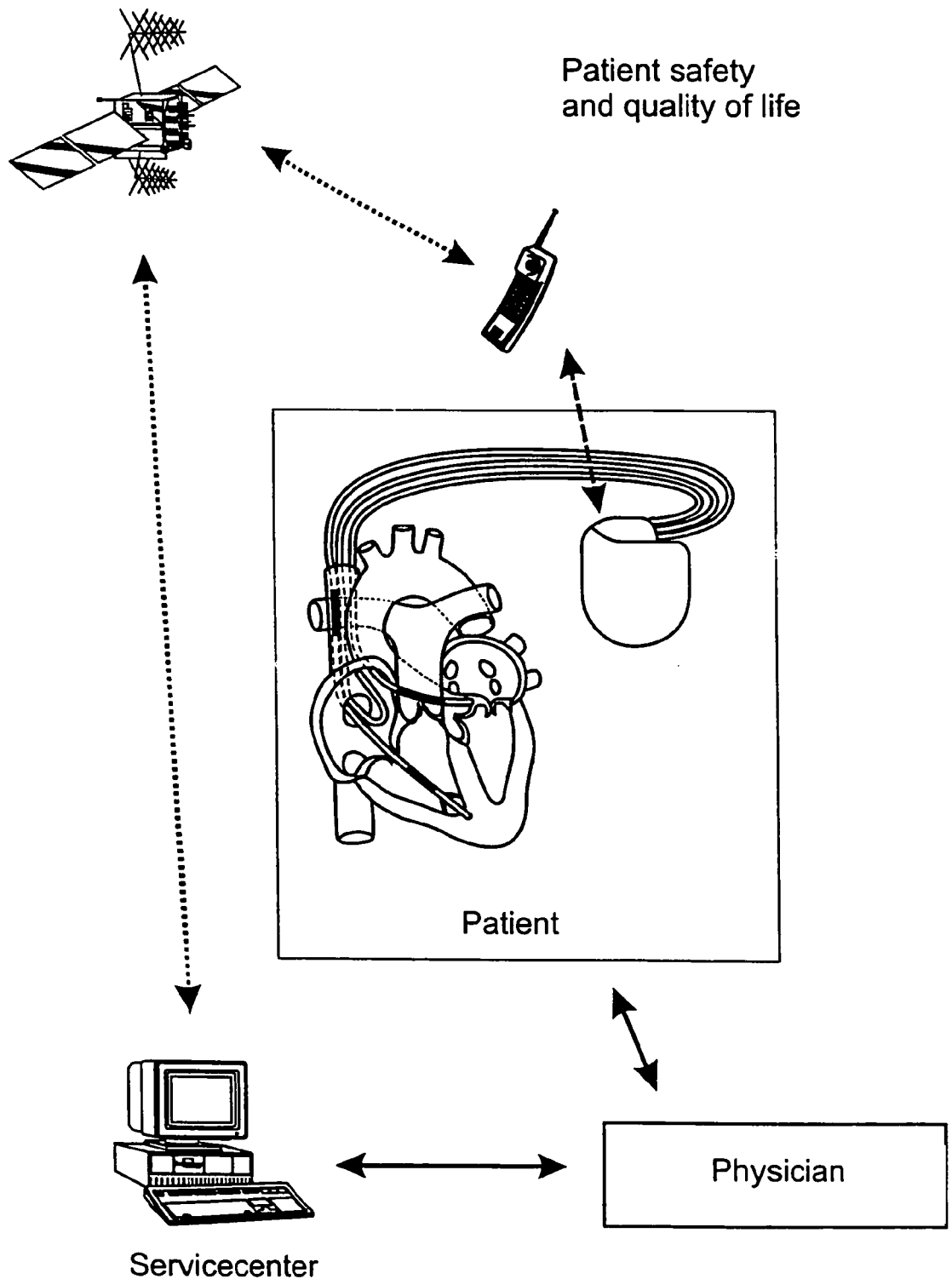
Figure 7M:
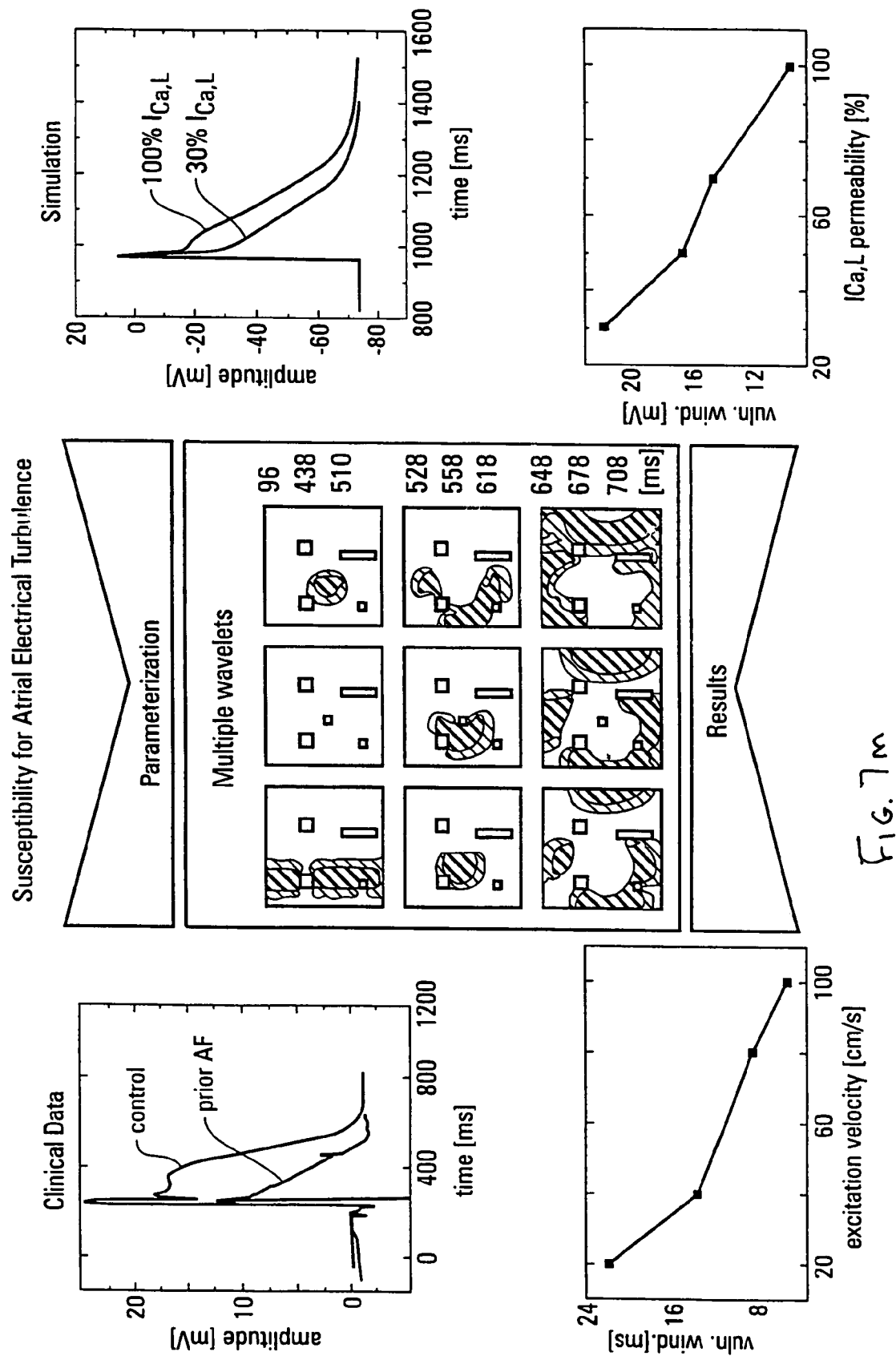

The further thirteen views, shown as FIGS. 7A through 7M, provide various systems designed in accordance with the invention in regard to their mode of operation or parts thereof. Notable among these is the first representation of the invention, as shown in FIG. 7A and a second representation, shown in FIG. 7B. In this embodiment, clinical observation parameter that are picked up by the sensors are combined in subsets to form a sort of meta-observable. The primary clinical observation parameters, such as pressure, stroke volume, contractility, inotropic reserves, ejection fraction, heart rate, heart rate variability, AV-interval, impedance data, respiratory data, repolarization time and ventricle evoked response are designated as $\alpha_1$ through $\alpha_n$. These clinical observation parameters are combined to provide a series of secondary or meta-observables, which are designated as $\beta_1$ through $\beta_n$. For example, FIG. 7A shows the combination of the clinical observation parameters of pressure, stroke volume and contractility to provide meta-observable $\beta_1$. These secondary observables are processed in order to determine which of them provide relevant information with respect to a future therapy liable event, such that a predictor signal can be derived from those relevant secondary observables. This determination of the relevant secondary observables is thus a self-learning process and is done, in one example, by determining which secondary observables are orthogonal with respect to each other. In doing this, it must be kept in mind that the secondary observables are themselves multi-dimensional vectors, because they comprise a combination of a plurality of primary or clinical observation parameters. The result, as shown in FIG. 7B, is the derivation of a plurality of diagnostic indices D, in a step called parameter extraction. The diagnostic indices are assigned to a plurality of therapy indices T. The therapy indices determine the therapy parameters that are to be applied by the implantable medical device. This process is recursive, as is shown by the directions of the arrows, because the application of any therapy that has an effect, either positive or negative, will lead to variation of at least some of the clinical observation parameters $\alpha_1$ through $\alpha_n$, which will in turn improve determination of the relevant secondary or meta-observables $\beta_1$ through $\beta_n$. In this manner, the self-learning process is advanced and the indicator signal and predictor signals are ascertained.

It will also be understood that additional primary observables used as input signals to derive the system output signal are arrhythmia indicators. These can include: the occurrence of extra systoles, the degree of prematurity of extra systoles, the number of premature cardiac contractions, arrhythmic patterns and conduction times within the ventricles.

The process of parameter extraction referred to above may be effected with at least one process which includes at least one of one- or multi-stage mathematical processes and filter means for finding a signal event in a signal mix. In such a case, at least one of the following may be provided as one of a mathematical processes and a filter means for finding a signal event in a signal mix: correlation, pattern comparison, comparison of the signal sets as status vectors using the least squares method, fuzzy logic, wavelets, non-linear linkages, Lorenz attractors, mathematical functions with a plurality of variables, and n-dimensional orthogonal systems. These mathematical operators may either be stored in the data memory 4 or may be accessed from an external source as needed. Such an external source may be the telemetry means shown in FIG. 7L.

It will be understood that the output signal derived from the process of the present invention may be one of three types. First, it may be a control signal that controls the operation of the therapy applicator. Second, it may be an indicator signal which represents a measurement of either a therapy-liable event or a therapy outcome. Third, it may be a predictor signal which represents a probability of either a future therapy-liable event or a future therapy outcome.

Regarding further possible structures and embodiments of the invention, attention is directed to the claims.

The invention is not limited in the implementation thereof to the above-described preferred embodiments which are set forth by way of example. On the contrary, it is possible to envisage a number of variants which make use of the illustrated solution, even in constructions of a different kind.

What is claimed is:

1. A medical therapy system for treatment of the heart with electrical pulses, comprising:
   at least one input side sensor;
   at least one output side therapy applicator;
   a data memory for storing patient, system condition and system configuration on data; and
   at least one linking/processing stage for processing indicator and predictor input signals connected between the at least one input-side sensor and the at least one output-side therapy applicator and in signal communication with the data memory;
   wherein time-dependent sensor input signals are received by the at least one linking/processing stage, and
   wherein the system has the capability to ascertain, from the sensor input signals and the data stored in the data memory, a control signal for controlling the operation of the therapy applicator, an indicator signal which represents a measurement of either a therapy-liable event or a therapy outcome, and a predictor signal which represents a probability of either a future therapy-liable event or a future therapy outcome, and wherein a system output signal is ascertained, the system output signal being selected from the group consisting of the control signal, the indicator signal, and the predictor signal, and
   wherein the system output signal additionally has a time reference signal which contains a predictor of the probable moment in time of the occurrence of the therapy-liable event or the therapy outcome.

2. The therapy system of claim 1, wherein the input signals are clinical observation parameters.

3. The therapy system of claim 2 wherein the clinical observation parameters are arrhythmia indicators.

4. The therapy system of claim 1, wherein the input signals for the derivation of system output signals arc arrhythmia indicators which can include the occurrence of extra systoles, the degree of prematurity of extra systoles, the number of premature cardiac contractions, arrhythmic patterns and conduction times within the ventricles.

5. The therapy system of claim 4, wherein at least one of the following is provided as one of a mathematical processes and a filter means for finding a signal event in a signal mix:
   correlation, pattern comparison, comparison of the signal sets as status vectors using the least squares method, fuzzy logic, wavelets, non-linear linkages, Lorenz attractors, mathematical functions with a plurality of variables, and n-dimensional orthogonal systems.

6. The therapy system of claim 1, wherein extraction of system output signals is effected with at least one process which includes at least one—or multi-stage mathematical processes and filter means for finding a signal event in a signal mix.

7. The therapy system of claim 1, wherein at least one sensor means, sensor signal is fed as an input signal to a first linking/processing stage, and a processed sensor signal appears as an output signal of the first linking/processing stage, and wherein the first linking/processing stage includes geometry evaluation of at least one of the sensor means and time and frequency correction of the sensor signals.

8. The therapy system of claim 1, further comprising:
   at least one linking/processing module comprising a plurality of linking/processing stages;
   wherein the module comprises a multi-usable processing and linking module which can be used as at least one of a first, second, third and fourth linking stage in time sequence, and
   wherein input signals, the nature of the input signals to be linked and processed, a processing algorithm and a linking algorithm can be fed to the linking/processing module.

9. The therapy system of claim 8, wherein the processing and linking module additionally has an item of linking information.

10. The therapy system of claim 9 wherein the item of linking information defines which input values are to be superimposed in what manner.

11. The therapy system of claim 8 wherein the linking algorithm, the processing algorithm or the combination thereof are formed by one of plug-ins and applets as additional processor or software portions, which are either disposed in the data memory or are loaded into the data memory as required by way of telemetry means from an external source.

12. The therapy system of claim 8 wherein the linking module is one of circuit or software.

13. The therapy system of claim 1, wherein the performance of a linking/processing stage is variable by means of the system data, which can be read into the memory.

14. The therapy system of claim 1 comprising a plurality of linking/processing stages which make up a processing/linking module.

15. The therapy system of claim 1 wherein the treatment of the heart comprises electrostimulation.

16. The therapy system of claim 1, wherein the stored data are empirical values extracted from a plurality of similar therapy cases.

17. A method of treating a heart with electrical pulses from a therapy system having an input side sensor, and output side therapy applicator, a data memory, and at least one processor between the sensor and applicator and in signal communication with the data memory, the processor having the capability to ascertain a control signal from the sensor input signals and the data stored in the data memory for controlling the operation of the therapy applicator, a time-dependent indicator signal which represents a measurement of either a therapy-liable event or a therapy outcome, and a predictor signal which represents a probability of either a future therapy-liable event or a future therapy outcome, the method comprising the steps of:

ascertaining a system output signal from input signals and stored data, which are put into the processor, the system output signal representing a signal selected from the group consisting of: the therapy applicator control signal, the time-dependent indicator, and the predictor signal;

forming a signal/data set having at least one of a reference time statement and a validity time range statement which characterizes one of a moment in time at which the signal/data set was received and a time validity range at which the signal/data set is valid, wherein the beginning and end of the validity range do not need to be fixed, and wherein the signal/data set contains at least one of output signals from the sensor, indicator signals, patient condition signals, therapy application signals, system description signals, input signals to the processor, output signals from the processor, and system configuration data;

transmitting data set by telemetry means to a remote data processing station in order of time references associated with the signal/data sets by at least one of the following operations:

reducing memory required by signal compression of signal/datasets according to the age of the signal/data set;

checking die signal/data sets for inconsistencies, and one of correcting and erasing the inconsistencies;

investigating dynamic stability of the system to detect unusual data/signal sets;

investigating operability of the system by switching the generation of the therapy signals over to a backup system if a deviation between the predicted and the actual therapy outcome is detected, and stopping the previously active system;

comparing at least part or the signal data sets that are associated with a predictor of the therapy-liable event or therapy outcome with at least part of the signal/data sets that are associated with an actual therapy-liable event or therapy outcome, wherein when a predetermined deviation between the two is detected, a predetermined change in at least one system condition parameter is made; and converting one of a frequency spectrum of the signal/data set into time-dependent signals and time-dependent signals of the signal data set into a frequency spectrum.

18. The method of claim 17 wherein the step of converting the signal/data set is by Past-Fourier or wavelet transformation.

19. A medical therapy system for treatment orate heart with electrical pulses, comprising:

at least one input side sensor;

at least one output side therapy applicator;

a data memory for storing patient, system condition and system configuration data; and at least one linking/processing stage for processing indicator and predictor input signals connected between the at least one input-side sensor and the at least one output-side therapy applicator and in signal communication with the data memory;

wherein time-dependent sensor input signals are received by the at least one linking/processing stage, and wherein the system has the capability to ascertain, from the sensor input signals and the data stored in the data memory, a control signal for controlling the operation of the therapy applicator, an indicator signal which represents a measurement or either a therapy-liable event or a therapy outcome, and a predictor signal which represents a probability of either a future therapy-liable event or a future therapy outcome, and wherein a system output signal is ascertained, the system output signal being selected from the group consisting of: the control signal, the indicator signal, and the predictor signal, and wherein the system output signal is a predictor signal which includes a probability evaluation parameter for the probability of the occurrence of the therapy-liable event or the therapy outcome.

20. A medical therapy system for treatment of the heart with electrical pulses, comprising:

at least one input side sensor;

at least one output side therapy applicator;

a data memory for storing patient, system condition and system configuration data; and at least one linking/processing stage for processing indicator and predictor input signals connected between the at least one input-side sensor and the at least one output-side therapy applicator and in signal communication with the data memory;

wherein time-dependent sensor input signals are received by the at least one linking/processing stage, and wherein the system has the capability to ascertain, from the sensor input signals and the data stored in the data memory, a control signal for controlling to operation of the therapy applicator, an indicator signal which represents a measurement of either a therapy-liable event or a therapy outcome, and a predictor signal which represents a probability of either a future therapy-liable event or a future therapy outcome, and wherein a system output signal is ascertained, the system output signal being selected from the group consisting of: the control signal, the indicator signal, and the predictor signal, and wherein at least a first and a second linking/processing stage, wherein at least one signal value from the first linking/processing stage is fed as an input signal to the second linking/processing stage, whose output signal forms the system output signal, and wherein the second linking/processing stage output signal forms the input signal of a third linking/processing stage, which produces an output signal that supplies a therapy applicator crude signal, and wherein the therapy applicator crude signal forms an input signal of a fourth linking/processing stage which supplies as its output signal a therapy applicator signal, wherein the fourth linking/processing stage includes geometry evaluation of at least one of the therapy application means, a time, and a frequency correction of the therapy applicator crude signal.

21. A medical therapy system for treatment of the heart with electrical pulses, comprising:
- at least one input side sensor;
- at least one output side therapy applicator;
- a data memory for storing patient, system condition and system configuration data; and
- at least one linking/processing stage for processing indicator and predictor input signals connected between the at least one input-side sensor and, the at least one output-side therapy applicator and in signal communication with the data memory;
- wherein time-dependent sensor input signals are received by the at least one linking/processing stage, and
- wherein the system has the capability to ascertain, from the sensor input signals and the data stored in the data memory, a control signal for controlling the operation of the therapy applicator, an indicator signal which represents a measurement of either a therapy-liable event or a therapy outcome, and a predictor signal which represents a probability of either a future therapy-liable event or a future therapy outcome, and wherein a system output signal is ascertained, the system output signal being selected from the group consisting of: the control signal, the indicator signal, and the predictor signal, and
- wherein at least one of the signals from or between the at least one input side sensor, the individual linking/processing stages, the memory, and the therapy applicator forms a signal/data set having at least one of a reference time statement and a validity time range statement which characterizes one of a moment in time at which the signal/data set was received an a time validity range at which the signal/data set is valid, wherein the beginning or the end of the validity range does not need to be fixed so that the signal/data set can be suitably taken into consideration or allocated in the subsequent processing operation, and
- wherein associated with the signal/data set is an alphanumeric identification which serves to identify and select the corresponding signal/data set.

22. The therapy system of claim 21 wherein the signal/data sets are stored in the data memory.

23. The therapy system of claim 21 wherein the reference time statement is one of a real time statement, a time statement which refers to a cyclic time period of a patient condition parameter, and a time statement which refers to a cyclic time period of a therapy parameter.

24. The therapy system of claim 21 wherein the signal/data set includes at least one of the following items of information: Boolean logic data, amplitude data, amplitude pattern data, spectral information data associated with the reference time, information relating to the geometrical arrangement of at least one of the sensor and application means, patient condition data, system configuration data, linking algorithms and processing algorithms.

25. The therapy system of claim 21 wherein a change in one of the input signals and signal/data sets for a linking/processing stage triggers an updating of the output signals of the linking/processing stage.

26. The therapy system of claim 25 wherein a condition fir triggering updating of the output signals of the linking/processing stage is the fulfillment of a condition for the reference time and time range information.

27. The therapy system of claim 21 wherein one of external processing and calculation of the system output is effected by the signal/data sets of a collection of similar signals with comparable signal/data contents and/or a patient model which is stored as data in the data memory.

28. The therapy system of claim 21 wherein one 6f the input of signals, data values of the signal/data set, and execution of calculations is provided from the exterior by way of telemetry.

29. The therapy system of claim 28 wherein the telemetry is provided at least in part by way of the Internet.

30. A medical therapy system for treatment of the heart with electrical pulses comprising:
- at least one input side sensor;
- at least one output side therapy applicator;
- a data memory for storing patient, system condition and system configuration data; and
- at least one linking/processing stage for processing indicator and predictor input signals connected between the at least one input-side sensor and the at least one output-side therapy applicator and in signal communication with the data memory;
- wherein time-dependent sensor input signals are received by the at least one linking/processing stage, and
- wherein the system has the capability to ascertain, from the sensor input signals and the data a stored in the data memory, control signal for controlling the operation of the therapy applicator, an indicator signal which represents a measurement of either a therapy-liable event or a therapy outcome, and a predictor signal which represents a probability of either a future therapy-liable event or a future therapy outcome, and wherein a system output signal is ascertained, the system output signal being selected from the group consisting of: the control signal, the indicator signal, and the predictor signal, and
- wherein at least one of the signals from or between the at least one input side sensor, the individual linking/processing stages, the memory, and the therapy applicator forms a signal/data set having at least one of a reference time statement and a validity time range statement which characterizes one of a moment in time at which the signal/data set was received an a time validity range at which the signal data set is valid, wherein the beginning or the end of the validity range does not need to be fixed so tat the signal/data set can be suitably taken into consideration or allocated in the subsequent processing operation, and the therapy system further comprising:
- at least one linking/processing module comprising a plurality of linking/processing stages;
- wherein a plurality of linking/processing stages or linking/processing modules, independently of or in coordination with linking/processing stages that are responsive to output signals of the sensor means, execute at least one of the following operations by data transmission using telemetry means to a remotely disposed data processing station in order of the time references associated with the signal/data sets;
- compressing the memory needed for the signal/data sets by reducing data associated with the signal/data sets by replacing more complex data structures with simpler structures by increasing age of the reference times associated with the signals/data using an additional processing and linking stage for compacting patient condition data by combining a plurality of signal data sets of patient condition data associated with various moments in time or periods of time to give patient condition data associated with a greater period of time, said compression effect being proportionally greater, the further back the moments in time or periods of time are in relation to the current system time, checking of the signal/data sets for possible inconsistencies, and correction of inconsistent data/signals or erasure thereof, implementing investigations in respect of dynamic stability of the system in the case of possible unusual data/signal conditions, implementing investigations in regard to operability of the system by switching over the generation of the therapy signals using one of an additionally provided backup and a conventional system in the event of a remaining deviation between predicted and occurred therapy outcome and stoppage of the previously active system, comparison of at least a part of the signal/data set which is associated with a predictor of the probably imminent, therapy-liable event or the therapy outcome, with the at least a part of the signal/data set associated with the therapy-liable event or the therapy outcome which actually occurred, and in the event of a predetermined deviation being exceeded, a change in at least one predetermined system condition parameter by a predetermined amount, and conversion of the frequency spectrum into time-dependent signals and vice versa of a signal data set.

31. The therapy system of claim 30 wherein the telemetry includes use of the Internet.

32. The therapy system of claim 30 wherein the conversion of the frequency spectrum into time-dependent signals is by Fast-Fourier or wavelet transformation.

33. A medical therapy system for treatment of the heart with electrical pulses, comprising:
    at least one input side sensor;
    at least one output side therapy applicator;
    a data memory for storing patient, system condition and system configuration data; and
    at least one linking/processing stage for processing indicator and predictor input signals connected between the at least one input-side sensor and the at least one output-side therapy applicator and in signal communication with the data memory;
    wherein time-dependent sensor input signals are received by the at least one linking/processing stage, and
    wherein the system has the capability to ascertain, from the sensor input signals and the data stored in the data memory, a control signal for controlling the operation of the therapy applicator, an indicator signal which represents a measurement of either a therapy-liable event or a therapy outcome, and a predictor signal which represents a probability of either a future therapy-liable event or a future therapy outcome, and wherein a system output signal is ascertained, the system output signal being selected from the group consisting of: the control signal, the indicator signal, and the predictor signal, and
    wherein at least one of the signals from or between the at least one input side sensor, the individual linking/processing stages, the memory, and to therapy applicator forms a signal/data set having at least one of a reference time statement and a validity time range statement which characterizes one of a moment in time at which the signal/data set was received an a time validity range at which the signal/data set is valid, wherein the beginning or the end of the validity range does not need to be fixed so that the signal/data set can be suitably taken into consideration or allocated in the subsequent processing operation, and
    wherein one of external processing and calculation of the system output as effected by the signal/data sets of a collection of similar signals with comparable signal/data contents and/or a patient model which is stored as data in the data memory.

34. A medical therapy system for treatment of the heart with electrical pulses, comprising:
    at least one input side senior;
    at least one output side therapy applicator;
    a data memory for storing patient, system condition and system configuration data; and
    at least one linking/processing stage for processing indicator and predictor input signals connected between the at least one input-side sensor and the at least one output-side therapy applicator and in signal communication with the data memory;
    wherein time-dependent sensor input signals are received by the at least one linking/processing stage, and
    wherein the system has the capability to ascertain, from the sensor input signals and the data stored in the data memory, a control signal for controlling the operation of the therapy applicator, an indicator signal which represents a measurement of either a therapy-liable event or a therapy outcome, and a predictor signal which represents a probability of either a future therapy-liable event or a future therapy outcome, and wherein a system output signal is ascertained, the system output signal being selected from the group consisting of: the control signal, the indicator signal, and the predictor signal, and
    wherein predictive processing for handling possibly occurring signal/data conditions is precautionarily effected according to at least one of the procedures selected from the group consisting of: interrupting the processing and discarding the acquired data/signals if prerequisites under which the predictive processing was effected no longer apply.

* * * * *